(12) United States Patent
Govil et al.

(10) Patent No.: US 10,660,986 B2
(45) Date of Patent: May 26, 2020

(54) BIOACTIVE GRAFTS AND COMPOSITES

(71) Applicant: Advanced Biologics, LLC, Carlsbad, CA (US)

(72) Inventors: Amit Prakash Govil, Carlsbad, CA (US); Christian Gamboa, San Diego, CA (US)

(73) Assignee: Advanced Biologics, LLC, Carlsbad, CA (US)

( * ) Notice: Subject to any disclaimer, the term of this patent is extended or adjusted under 35 U.S.C. 154(b) by 0 days.

(21) Appl. No.: 15/654,830

(22) Filed: Jul. 20, 2017

(65) Prior Publication Data

US 2017/0312386 A1 Nov. 2, 2017

Related U.S. Application Data

(63) Continuation-in-part of application No. 15/252,737, filed on Aug. 31, 2016, now abandoned, which is a continuation of application No. 14/598,681, filed on Jan. 16, 2015, now abandoned, which is a continuation of application No. 12/959,777, filed on Dec. 3, 2010, now abandoned, which is a continuation-in-part of application No. 12/636,751, filed on Dec. 13, 2009, now abandoned.

(60) Provisional application No. 61/201,612, filed on Dec. 13, 2008, provisional application No. 61/240,283, filed on Sep. 7, 2009.

(51) Int. Cl.

| *A61F 2/46* | (2006.01) |
| *A61L 27/54* | (2006.01) |
| *A61L 27/50* | (2006.01) |
| *A61L 27/36* | (2006.01) |
| *A61K 35/32* | (2015.01) |
| *A61L 27/38* | (2006.01) |
| *A61K 35/28* | (2015.01) |
| *A61L 27/20* | (2006.01) |
| *A61L 27/12* | (2006.01) |
| *C08L 5/08* | (2006.01) |

(52) U.S. Cl.
CPC ............ *A61L 27/20* (2013.01); *A61F 2/4644* (2013.01); *A61K 35/28* (2013.01); *A61K 35/32* (2013.01); *A61L 27/12* (2013.01); *A61L 27/365* (2013.01); *A61L 27/3608* (2013.01); *A61L 27/3821* (2013.01); *A61L 27/3834* (2013.01); *A61L 27/50* (2013.01); *A61L 27/54* (2013.01); *C08L 5/08* (2013.01); *A61F 2002/4646* (2013.01); *A61L 2300/232* (2013.01); *A61L 2300/404* (2013.01); *A61L 2300/406* (2013.01); *A61L 2300/412* (2013.01); *A61L 2300/45* (2013.01); *A61L 2300/60* (2013.01); *A61L 2300/62* (2013.01); *A61L 2400/16* (2013.01); *A61L 2430/02* (2013.01)

(58) Field of Classification Search
None
See application file for complete search history.

(56) References Cited

U.S. PATENT DOCUMENTS

| 6,478,825 B1* | 11/2002 | Winterbottom ........... A61F 2/28 623/23.63 |
| 2003/0158302 A1* | 8/2003 | Chaput ................ A61K 9/0019 524/115 |
| 2007/0202191 A1* | 8/2007 | Borden ................. A61L 27/222 424/549 |

* cited by examiner

*Primary Examiner* — Leslie Lopez
(74) *Attorney, Agent, or Firm* — Thomas|Horstemeyer, LLP

(57) ABSTRACT

Disclosed are various bioactive and/or biocompatible materials and methods of making the same.

12 Claims, 16 Drawing Sheets

| Measurements | Average Material Density: 41.13% | Average Material Density: 20.42% |
|---|---|---|
| Total Volume (mm³) | 844.8 | 843.8 |
| Material Volume (mm³) | 347.5 | 172.3 |
| Empty Space Volume (mm³) | 497.3 | 671.5 |
| ROI (mm) | 7.5x7.5x15.02 | 7.5x7.5x15 |

FIG. 14

BIOACTIVE GRAFTS AND COMPOSITES

CROSS-REFERENCE TO RELATED APPLICATIONS

This application is a continuation in part of U.S. patent application Ser. No. 15/252,737 entitled "BIOACTIVE GRAFTS AND COMPOSITES," filed on Aug. 31, 2016, which is a continuation of U.S. patent application Ser. No. 14/598,681 entitled "BIOACTIVE GRAFTS AND COMPOSITES," filed on Jan. 16, 2015, which is a continuation of U.S. patent application Ser. No. 12/959,777 entitled "BIOACTIVE GRAFTS AND COMPOSITES," filed on Dec. 3, 2010, which is a continuation in part of U.S. patent application Ser. No. 12/636,751 entitled "BIOACTIVE GRAFTS AND COMPOSITES," and filed on Dec. 13, 2009, which claims the benefit of U.S. Provisional Application Ser. No. 61/240,283 entitled "BIOACTIVE ALLOGRAFTS AND COMPOSITES," filed Sep. 7, 2009 and U.S. Provisional Application Ser. No. 61/201,612 entitled "STIMULATIVE GROWTH AGENTS DERIVED FROM PHYSIOLOGICAL FLUIDS AND METHOD OF MAKING," filed Dec. 13, 2008, the contents of which are expressly not incorporated by reference.

BACKGROUND

Grafts and implants derived from or including various tissues can be employed in patients suffering from disease and disorders or otherwise in need of reconstructive procedures. Given the myriad applications for grafts and implants, there exists a need for the development of grafts and implants suitable for those varied applications.

BRIEF DESCRIPTIONS OF THE DRAWINGS

Many aspects of the present disclosure can be better understood with reference to the following drawings. The components in the drawings are not necessarily to scale, emphasis instead being placed upon clearly illustrating the principles of the disclosure. Moreover, in the drawings, like reference numerals designate corresponding parts throughout the several views.

FIG. 14 is a table illustrating examples of material properties in accordance with various embodiments of the present disclosure.

DETAILED DESCRIPTION

Figure 1:
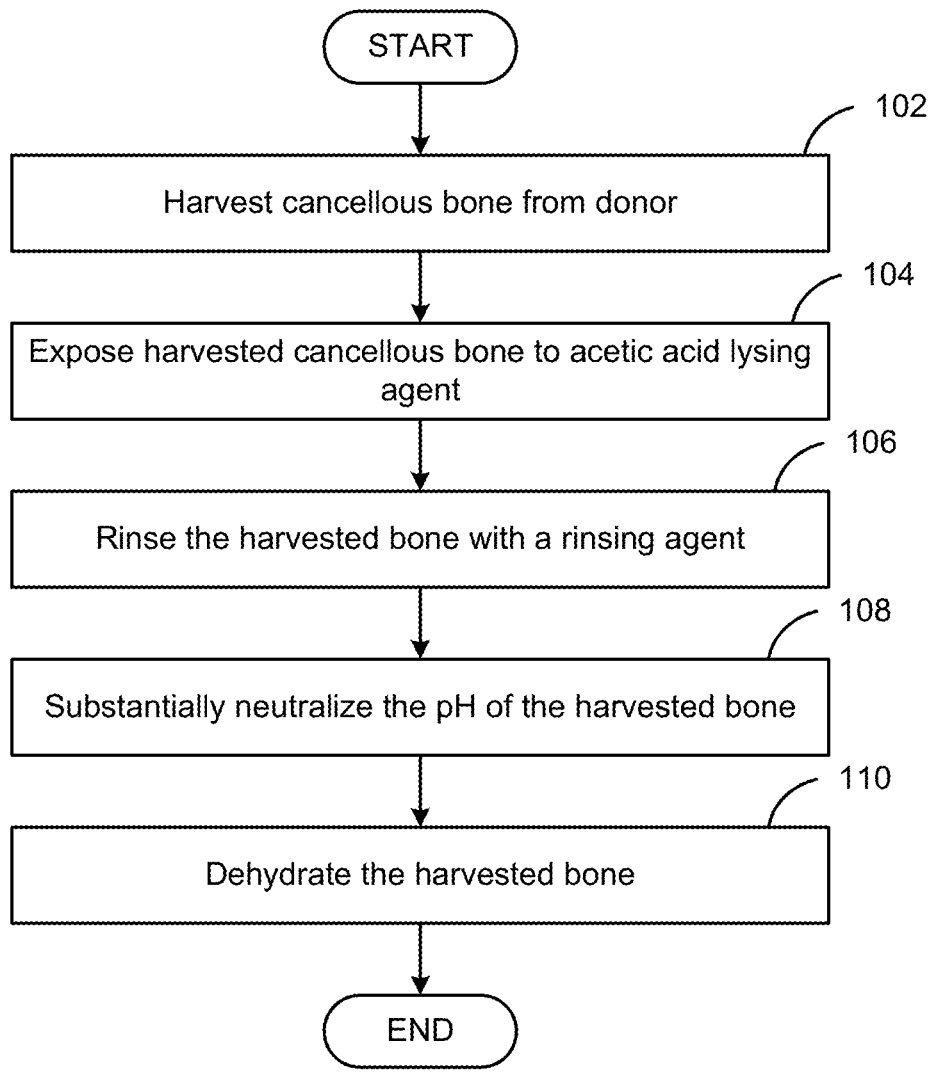
FIG. 1 is a flow diagram illustrating one embodiment in accordance with the present disclosure.

Various embodiments of the present disclosure relate to bioactive factors and/or biocompatible materials that stimulate tissue growth. As can be appreciated these bioactive factors can be derived from physiological solutions containing cells. Physiological solutions may exist as solutions naturally in the body or be derived from tissue when the cells are extracted. Any tissue containing cells may be a source of physiological fluid, such as, for example, mesodermal, endodermal, and ectodermal tissues. Examples of these tissues include bone marrow, blood, adipose, skin, muscle, vasculature, cartilage, ligament, tendon, fascia, pericardium, nerve, and hair. These tissues may also include organs such as the pancreas, heart, kidney, liver, intestine, stomach, and bone. The cells may be concentrated prior to processing as described by the current disclosure.

In accordance with one embodiment, a portion of cancellous, corticocancellos and/or cortical bone or any combination thereof can be harvested from a donor. In one embodiment, the harvested material can be harvested in such a way as to retain as much bone marrow in the harvested sample as possible.

The harvested sample can be exposed to lysing conditions and/or a lysing agent to facilitate lysis of the cells therein to release growth factors and nutrients contained sample. In other words, the harvested sample can be exposed to a lysing agent that lyses the cells within the harvested sample. Once cellular components are lysed, they release growth factors and/or bioactive materials, such as cytokines and nutrients, to stimulate growth, differentiation, and repair. These growth agents can be cytokines such as proteins, hormones, or glycoproteins including members of the TGF-β family (including bone morphogenetic proteins), interleukins, interferons, lymphokines, chemokines, platelet derived growth factors, VEGF, and other stimulative agents that promote growth, repair or regenerate tissues.

In other embodiments, cells from other tissues can be lysed to release growth agents that can be binded to the harvested sample and further processed as an implant. Lysing conditions may be mechanical in nature such as thermolysis, microfluidics, ultrasonics, electric shock, milling, beadbeating, homogenization, french press, impingement, excessive shear, pressure, vacuum forces, and combinations thereof. Excessive shear may be induced by aggressive pipetting through a small aperture, centrifuging at excessive revolutions per minute resulting in high gravity forces. Rapid changes in temperature, pressure, or flow may also be used to lyse cellular components. Lysing conditions can include thermolysis techniques that may involve freezing, freeze-thaw cycles, and heating to disrupt cell walls. Lysing conditions can also include microfluidic techniques that may involve osmotic shock techniques of cytolysis or crenation.

Lysing conditions can also include the imposition of ultrasonic techniques, including, but not limited to, sonication, sonoporation, sonochemistry, sonoluminescence, and sonic cavitation. Lysing conditions can also include electric shock techniques such as electroporation and exposure to high voltage and/or amperage sources. Lysing conditions can further include milling or beat beating techniques that physically collide or grind cells in order to break the cell membranes, releasing the stimulative agents contained within.

Lysing can also be accomplished by exposing cells of the harvested sample to a lysing agent, which can facilitate release of stimulative growth agents include lysis due to pH imbalance, exposure to detergents, enzymes; viruses; solvents, surfactants; hemolysins, and combinations thereof. Chemical induced lysis of the cells by pH imbalance may involve exposure of cells of the harvested sample to a lysing agent in order to disrupt the cell walls and release soluble growth agents. In some embodiments, a lysing agent can include one or more acids and/or bases.

After exposure to the lysing agent; the harvested sample may be exposed to buffers or other solutions to substantially neutralize the pH of the mixture of the growth factors and the lysing agent. In some embodiments, it may be desired that the pH be acidic (e.g., pH below 7) or basic (e.g., pH above 7) to retain solubility of particular growth factors or bioactive agents. For example, bone morphogenetic proteins (particularly BMP-2, BMP-4; BMP-6, BMP-7, BMP-9, BMP-14, and other bone morphogenetic proteins 1-30) are more soluble at acid pH values under 7 than neutral or basic pH.

In other embodiments, a lysing agent can include a volatile acid or base, such as acetic acid or ammonia, and the cellular material, after exposure to the lysing agent, may be neutralized or partially neutralized by drying techniques such as evaporation, vacuum drying, lyophilization, freeze drying, sublimation, precipitation, and similar processes as can be appreciated. In yet other embodiments, a lysing agent can include detergents that can disrupt cell walls and remove any lipid barriers that may surround the cell. Enzymes, viruses, solvents, surfactants, and hemolysins can also help cleave or remove outer cell membranes releasing the bioactive growth agents contained within.

The use of these lysing agents and/or exposure of the harvested sample to lysing conditions may be followed by neutralization, as noted above, and/or another secondary process to remove any undesired remnants. The growth agents, nutrients, etc., released by the lysing process may be added to a carrier such as a synthetic scaffold, non-bone biologic scaffold (e.g. collagen or other non-bone tissue scaffold). In yet other embodiment, a harvested non-bone sample, acting as a carrier can be exposed to lysing conditions and/or a lysing agent, and bioactive factors released by the lysing process can be binded to at least a portion of the sample. In some embodiments, the growth agents released by lysing of cellular material may be used immediately for autologous use. In other embodiments, the released growth agents may be stored for allogenic use (e.g. separately from the tissue they were derived from) Storage techniques can include freezing or lyophilization to preserve bioactivity. The growth factors and nutrients may also be frozen or lyophilized on the chosen carrier to allow for complete binding of the stimulative agent to the carrier and to allow for immediate use by the surgeon. Lyophilization also allows for greater room temperature shelf life and an opportunity for concentration into a smaller volume.

Another embodiment of the present disclosure relates to obtaining a specific set of growth factors and nutrients from a physiological solution containing cells. In this embodiment, cells are lysed as described above and the lysate solution is subjected to materials with a charged surface, including, but not limited to, chromatography resins, ceramics, soft tissues, and other materials with an electric charge. The charged surface attracts certain stimulative growth agents and molecules removing them from the lysate solution. The remaining growth agents can then be used to regenerate or repair the desired tissue type. Similar to the previous embodiment, the growth agent solution can be further concentrated and frozen or lyophilized in order to extend shelf life.

Another embodiment of the disclosure includes selectively rinsing, lysing, or removal of certain cellular components while retaining other cellular components. Selective lysing or removal can be accomplished physically by methods described above. As can be appreciated, certain cells can be resistant to various lysing mechanisms. As a non-limiting example, mesenchymal stem cells (MSC) are resistant to cytolysis and osmotic lysis due to their resistant cell walls and ineffective cells volumes. Accordingly, to accomplish selective lysing, osmotic lysis can be used to lyse red and white blood cells from blood or bone marrow. Once the non-resistant cells are lysed, the resulting solution is an enriched MSC population. The solution can then be further concentrated via centrifugation, florescence-activated cell sorting (FACS), filtration, magnetic bead selection and depletion, and/or gravity sedimentation. For allogeneic transplantation, FACS and magnetic bead separation and depletion can be useful in removing any remaining cells that would cause an immune response from the implant patient. Once implanted, cells can function in a homologous manner and differentiate in the desired phenotype.

Another embodiment of the disclosure includes a combination of previous two embodiments. A physiological solution may be enriched by selective lysis and further concentrated by centrifugation, FACS, magnetic bead selection and depletion, and/or gravity sedimentation. The enriched physiological solution is added to a physiological solution that has been lysed in the methods described previously in order to help induce differentiation of the cells into the desired phenotype. These cells can then function in the desired manner to regenerate and repair tissues.

In another embodiment, cancellous bone may be exposed to a weak lysing agent (such as less than 1M acetic acid) that only partially lyses the cell population present. In this embodiment, the partial lysis releases growth factors and binds them to the bone while other cells, such as mesenchymal stem cells and progenitor cells, may still remain viable and attached to the bone.

In another embodiment, cancellous bone may be exposed a weak lysing agent (such as water) and then subjected to mechanical lysing conditions previously stated (such as thermolysis, high/low pressure, sonication, centrifugation, etc.). Once the cells have lysed, the bone, cell fragments, and debris are removed from the solution containing the growth factors. The solution may then become positively charged by the addition of an acid or another proton donor fluid. The growth factors in the solution may then be further concentrated using techniques described, frozen, or lyophilized into a soluble powder. The soluble powder could be reconstituted with a fluid prior adding it to an implant during surgery or added in the dry powder form to an implant prior to implantation.

In another embodiment, a bioactive factor (e.g. a growth factor) can be formed from non-bone physiological fluids containing cells. The cells can be lysed as described elsewhere herein. The bioactive factors released can be retained and stored and/or loaded onto a carrier.

In another embodiment, a physiological fluid containing cells, such as synovial fluid, may be harvested from a live donor, cadaveric donor, or autologously. The fluid may be subjected to mechanical or chemical lysing conditions described in order to solubilize growth factors. Once the growth factors are released from the cells, the solid materials (such as cells fragments, debris, or platelets) may be removed by processes described such as filtration, centrifugation, or gravity sedimentation. Once the solid materials are removed, the solution may be then become positively charged by the addition of an acid or another proton donor fluid. The growth factors in the solution may then be further concentrated using techniques described, frozen, or lyophilized into a soluble powder. The soluble powder could be reconstituted with a fluid prior adding it to an implant during surgery or added in the dry powder form to an implant prior to implantation. Alternatively, cartilage with or without synovial fluid can be prepared in a similar fashion for the repair and regeneration of cartilage or spinal discs. In addition, other tissues such as muscle, adipose, nerve, dermis, cardiac tissue, vascular tissue, nucleus pulposus tissue, annulus fibrosus tissue, or other solid tissues can be prepared in this fashion to be used to help repair or regenerate tissues.

Stimulative growth agents can be derived from various cellular solutions. These solutions may comprise cultured and/or uncultured cells, and can be autologous, allogeneic, or xenogeneic in origin. If the cells are allogeneic or xenogeneic in origin, at least partial lysing or immune cells depletion by methods previously described can be performed so that the stimulative growth agents do not elicit an immune response in the patient. Alternatively, immune response agents, such as CD45+ cells and other leukocytes, may be removed prior to use to reduce or eliminate immune response. These immune response agents may be removed by the selective lysing as previously described in this disclosure.

Various embodiments of the present disclosure relate to compositions and/or methods for providing an anti-microbial polysaccharide scaffold that may be combined with an osteostimulative agent such as bioactive growth factors and different types of cells to stimulate tissue growth, cell adhesion, cell proliferation, and enhanced wound healing. Chitosan is a polysaccharide found in marine crustacean shells and the cell walls of bacteria and fungi. Chitosan is a non-toxic biocompatible material that can support tissue growth. With the combination of biocompatibility, antibacterial activity, versatility in processing, and ability to bind cells and growth factors, chitosan is a distinguished biomaterial to support in tissue growth. The materials including viable cells may be customized for use within the applications such as, but not limited to; void fillers and implants for tissues or bone. hemostatic agent, wound covering, osteoncology, and treatment of infected site. The scaffold may also include minerals.

In one embodiment, a biocompatible shape memory osteoconductive and/or osteoinductive anti-microbial compressible implant scaffold may be used in tissue engineering. For example, the present disclosure provides an orthopedic structure comprising a chitosan solution and a non-toxic mineral mixture resulting in a compressible solid porous substrate.

The scaffold may comprise chitosan with a weight percentage in the range of about 5% to about 80%, in the range of about 10% to about 70%, and/or in the range of about 15% to about 60%. In some embodiments, the chitosan concentration is greater than about 5%, greater than about 30%, or more. In other embodiments, the chitosan concentration is less that about 10% or less than about 2.5%.

In accordance with various implementations of the present disclosure, the chitosan molecular weight may be in a range of between about 1 kDa and about 750 kDal, in a range of between about 10 kDal and about 650 kDa, and/or in a range of between about 50 kDa and about 550 kDa.

The chitosan used may be deacetylated chitosan. According to one implementation, the degree of deacetylation may range from, but is not limited to, about 50% to about 99% deacetylation. Generally, the lower the percentage/degree of deacetylation, the more rapid the degradation takes place when implanted. The deacetylation percentages may also be tailored to specific tensional and compressive properties. The lower the deacetylation the lower the tensile strength of the scaffold.

In accordance with various implementations, the deacetylation percentage of the chitosan can be in a range from about 50% to about 66.6% in order to produce more rapid degradation profile and in turn have a lower density affecting porosity. In other implementations, the deacetylation percentage of the chitosan can be in a medium range from about 66.6% to about 83.2% in order to produce a medium degradation profile and in turn have a medium density affecting porosity. In accordance with yet other implementations, the deacetylation percentage of the chitosan can be in a medium range from about 83.2% to about 99% in order to produce a longer degradation profile and in turn have a higher density affecting porosity.

The chitosan material may be compounded with an additional protein or amino acid to improve protein and cell binding. Examples of proteins, enzymes, structural proteins, cell signaling or ligand binding proteins, or amino acids include, but are not limited to, collagen, glutamic acid, and lysine. The chitosan may be medical grade or may be of equivalent quality containing low level of toxic contaminants such as heavy metals, endotoxins and other potentially toxic residuals or contaminants.

In accordance with various embodiments of the present disclosure, the chitosan solution can be prepared by dissolution in low pH fluids, such as acids. Low pH fluids include, but are not limited to, acetic, hydrochloric, phosphoric, sulfuric, nitric, glycolic, carboxylic, or amino acids. The amount of acid used may be between about 0.1% to about 50%, and/or may be between about 0.1% and about 25%. In some embodiments, the pH can range from slightly acidic to neutral or partially neutral. Neutralization can be obtained by using base substances such as, but not limited to, sodium hydroxide, ammonia hydroxide, potassium hydroxide, barium hydroxide, caesium hydroxide, strontium hydroxide, calcium hydroxide, lithium hydroxide, rubidium hydroxide, butyl lithium, lithium diisoprpylmadie, lithium diethylamide, sodium amide, sodium hydride, and lithium bis(trimethylsily)amide. Neutralization may also be obtained by using basic amino acids including lysine, histidine, methyllysine, arginine, argininosuccinic acid, L-arginine L-pyroglutamate, and ornithine. Different techniques to achieve neutralization may be used such as evaporation, vacuum drying, lyophilization, freeze drying, sublimation, precipitation, and similar process as can be appreciated. The resulting solution results in a suspension or gel comprising chitosan with a liquid medium being at least partially comprised of water. The suspension or gel may also include mineral particles.

The resultant chitosan/mineral suspension may then be shaped to desired forms such as porous solids or semisolids through techniques such as injection molding, vacuum molding, injection compression molding, rotational molding, electrospinning, 3D printing, casting, and phase separation. The shapes may be orthopedic shapes such as, for example, dowels, tubes, pins, screws, plates, wedges anchors, strips, bands, hooks, clamps, washers, wires, fibers, rings, sheets, spheres, and cubes.

In accordance with another aspect of the disclosure, the chitosan scaffold may have a matrix porosity ranging from about 1 μm to about 5 mm. The matrix scaffold may also have a different surface porosity compared to its internal porosity. The surface porosity may have ranges from about 1 μm to about 1 mm, while the internal porosity may range from about 10 μm to about 5 mm. Overall pore size can be dependent on concentrations of chitosan, lower concentrations will result in larger pore size while higher concentration will result in smaller pore size. Pores size may also be designed to align vertically, longitudinally, horizontally, or a combination thereof depending on the process used during preparation or the intended site of implantation. Size and direction of the pores and channels may be designed and controlled through control rate freezing, and directional freezing. Variables such as freezing rate, freezing temperature, and specified area of freezing can be changed to adjust pore/channel size and direction due to the functions of the temperature gradient. An implant can be frozen at a ramp down rate of −0.1° C. to −15° C. every 1 minute to 20 minutes, creating uniform crystal formation. After freeze drying, the crystals evaporate leaving pores within the implant. For example, a slow ramp down rate of −10° C. every 10 minutes will result in larger pore size, while a fast ramp down rate of −10° C. every 1 minute results in smaller pore size. Channels instead of pores can be formed by decreasing the ramp down rate even further to −5° C. every 15 minutes. Pore and/or channel directionality can designed by applying the freezing source during freeze drying to a specified area of the implant. For example, if the freezing source is applied to a specified area (e.g., a specific surface) of the implant, the pore or channel direction will be perpendicular to the freezing source. A combination of applied freezing sources can result in multidirectional pore or channel structure. If the freezing source is not placed in any specified area, then the pore or channel direction can be anisotropic.

In accordance with another aspect of the present disclosure, the implant may have shape memory once hydrated with liquid. A dehydrated or hydrated sponge may be compressed circumferentially, unilaterally, or in multiple directions up to about 10 times its original size but when hydrated goes back to its original shape. The scaffold can be compressed into various shapes such as, but not limited to, tubes, pins, cubes, strips, and sheets. Compression may occur externally directed towards the scaffold or internally directed outward from the scaffold.

In some embodiments, the biocompatible implant may include minerals such as calcium salts (e.g., calcium phosphate), silicate, carbonate, sulfate, halide, oxide sulfide phosphate, metals or semimetals including gold silver copper, alloys, and/or a combination thereof. In accordance with one aspect of the present embodiment, calcium phosphate may be selected from hydroxyapatite (HA), silicate hydroxyapatite (HA), tri-calcium phosphate (TCP), pure/substituted beta tri-calcium phosphate (β-TCP), alpha tri-calcium phosphate (α-TCP), octalcalcium phosphate (OCP), tetralcalcium phosphate (TTCP), dicalcium phosphate dehydrate (DCPD), and/or a combination thereof. Mineral particle sizes may range from a powder of about 1 nm to about 1 mm. The mineral content can also be added in a granule size ranging from about 50 μm up to about 5 millimeters. The implant may include granules larger than 100 μm to increase compression resistance and cell/protein binding.

The calcium salt concentration may be greater than about 10%, greater than about 30%, or greater than about 40%.

The scaffold may comprise a mineral in a range of about 5% to about 75%, in a range of about 8% to about 72%, and/or in a range of about 10% to about 70%.

In accordance with yet another aspect of the disclosure, the implant contains antimicrobial and/or antibacterial properties which are dependent on the amount of chitosan and pH levels that are used in the formulation. The chitosan concentration along with the pH can provide antimicrobial activity against but not limited to the following organisms; *staphlyococcus aureus* (MRSA), *Enterococcus faecalis* (VRE), *Acinetobacter baumanii, Escherichia coli, Klebsiella pneumoniae, Streptococcus pyogenes, Staphylococcus epidermidis, Alomonella choleraesuis, Pseudomonas aeruginos, Enterococcus faecalis, Serratia marcescens, Stenotrphomonas maltophilia, Streptococcus mutans, Clostrium difficle, Streptococcus pneumoniae, Shigella* species, *Enterobacter aerogenes, Proteus mirabilis, Proteus vulgaris, Citrobacter freundii, Enterobacter cloacae, Moraxella catarrhalis, Micrococcus luteus*, and *Vibrio cholera*. The material also increases in stiffness after an increase in pH. In some embodiments, the chitosan solution can range from about 5 mg/mL to about 200 mg/mL. The pH level may be less than 8 and/or less than 7.

In accordance with various embodiments, the scaffold tensile, torsional, shear, and compressive properties can be strengthened by crosslinking using methods such as, dehydrothermal, chemical, physical, or photometric crosslinking. Dehydrothermal crosslinking may involve exposing the scaffold to elevated temperatures with or without the use of negative pressure. Chemical crosslinking may include treatment with nitrous acid, malondiadehyde, psoralens, aldehydes, formaldehydes, gluteraldehydes, acetalaldehyde, propionaldehyde, butyraldehyde, bensaldehyde, cinnamaldehyde, and/or tolualdehyde. Photometric crosslinking may use energy and/or light sources that may include ultraviolet, plasma, or other energy sources.

In various embodiments, a biocompatible osteoconductive and/or osteoinductive anti-microbial implant scaffold may be used use in tissue engineering. An orthopedic structure comprising a chitosan solution includes one or more substances including growth factors, growth factor stimulative agents, vitamins, and/or biologically active molecules. Calcium salts (e.g., calcium phosphate) may also be included as an osteostimulative agent.

Growth factors in the materials having viable cells can include, but are not limited to, bone morphogenetic protein (BMP), transforming growth factor β (TGF-β), growth differentiation factor (GDF), cartilage derived morphogenetic protein (CDMP), interleukins, interferon, lymphokines, chemokines, platelet derived growth factors (PDGF), VEGF, β-fibroblast growth factor (β-FGF), fibroblast growth factors (FGF), and other stimulative agents that promote growth, repair or regenerate tissue. Bone morphogenetic protein may be selected from BMP-2, BMP-3, BMP-4, BMP-5, BMP-6, BMP-7, BMP-8, BMP-9, BMP-10, BMP-11, BMP-12, BMP-13, BMP-14, BMP-15, and BMP-16. The bone morphogenetic protein may also be recombinant human bone morphogenetic protein. Growth factors may also be angiogenic or mitogenic growth factors.

In another embodiment, a biocompatible osteoconductive and/or osteoinductive anti-microbial implant scaffold may be used in tissue engineering. An orthopedic structure comprising a chitosan solution and a mineral mixture includes seeded cells. The cells can comprise of mesenchymal stems cell (MSC), adipocytes, chondrocytes, osteocytes, fibroblasts, osteoblasts, preosteoblasts, osteprogenitor cells, and combinations thereof.

In various embodiments, a biocompatible osteoconductive and/or osteoinductive anti-microbial malleable implant scaffold may be used in tissue engineering. An orthopedic structure comprising a chitosan solution and a mineral mixture has a putty-like consistency. The material may be molded to meet different situations. Formulation parameters may be adjusted to have different viscosities and adhesion characteristics based on the application.

In alternative embodiments, a biocompatible osteoconductive and/or osteoinductive anti-microbial flowable implant scaffold may be used in tissue engineering. An orthopedic structure comprising a chitosan solution and a mineral mixture has a flowable consistency. The material may be tailored to meet different situations. Viscosity parameters may be formulated to have less viscous properties in applications such as pastes, injectable gels and sprays. The paste and gels can be applied into the body in the desired shape, to aid in the efficacy of the application. A less viscous formulation such as putty or a very viscous injectable/flowable fluid can be applied in places such as bone voids, bioinert implants, cannulated screws, around screws, or other orthopaedic applications.

In various other embodiments, a biocompatible osteoconductive and/or osteoinductive anti-microbial coating implant scaffold may be used in tissue engineering. An orthopedic structure comprising a chitosan solution and a mineral mixture has a low viscosity consistency for coating purposes. The coating may be applied to bioinert materials such as, but not limited to, peek, stainless steel, titanium, radel, and silicone structures. For example, a coating can be applied to (e.g., sprayed on) bioinert implants such as, but not limited to, cages, screws, screw heads, pins, rods, wires, dowels, connectors, hip stems, acetabular cups, and plates. A coating may also be applied to (e.g., sprayed on) bioactive implants such as, but not limited to, minerals, autograft, allograft, xenograft, and collagen.

The systems and methods described herein can be employed in surgical environments where the implantation of stimulative growth agents in a patient is desired. Although the present disclosure describes the methods and systems for producing stimulative growth agents, particularly ones derived from physiological fluids containing cells or cellular tissues, it is understood that the methods and systems can be applied for a wide variety of medical applications including ones directed at regeneration or repair of bone, cartilage, muscle, tendon, ligament, vasculature, fat, annulus fibrosus, nucleus pulposus, skin, hair, blood, lymph nodes, fascia, neural, cardiac, pancreatic, hepatic, ocular, dental, digestive, respiratory, reproductive, and other soft tissue applications, such as in regenerative medicine and tissue engineering.

Reference is now made to FIG. 1, which depicts a method in accordance with one embodiment of the disclosure. In the embodiment illustrated in FIG. 1, an implant that can be suitable for bone applications is shown. In the embodiment of FIG. 1, cancellous bone is recovered from a cadaver, live donor, or harvested autologously from a patient in box 102. The harvested cancellous bone can be ground or cut to a desired shape and configuration as can be appreciated. Care may be taken to retain some cellular material, bone marrow, and/or blood within the bone during harvest and cutting operations. In prior art implants, bone marrow and/or blood within the bone can be systematically removed and/or cleaned from the harvested bone sample. In an embodiment of the disclosure, cancellous bone may have cortical bone portions such as in the iliac crest, vertebral bodies, chondyles, etc.

The cancellous bone is then exposed to acetic acid in box 104, which acts as a lysing agent as described above. In one embodiment, the acetic acid concentration can be greater than/%, in a molarity range of 0.2M-17M. The acetic acid lysing agent is employed to lyse cells remaining in the porous bone structure and on bone surface of the cancellous bone. The lysing of the cells releases and solubilizes growth factors and bioactive materials contained in the cellular material. Additionally, pH of the harvested bone may be substantially neutralized in box 108. In some embodiments, the pH of the harvested bone can be neutralized by the rinsing agent and rinsing step in box 106. In other embodiments, pH neutralization may not be required. Further pH neutralization of the harvested bone may be accomplished by dehydrating in box 110 by evaporation, vacuum drying, or lyophilization to reduce the acetic acid lysing agent to a residue and bring the implant to a more neutral pH.

Figure 2:
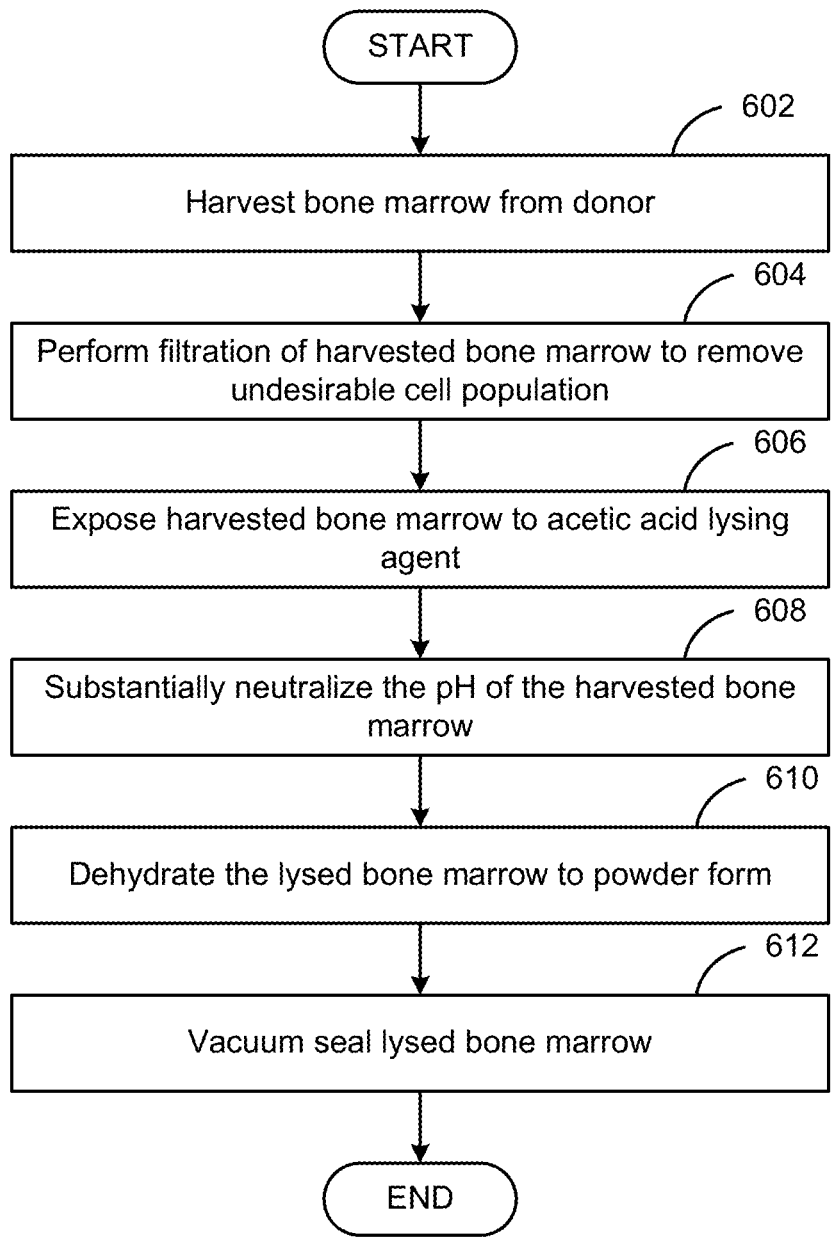
FIG. 2 is a flow diagram illustrating one embodiment in accordance with the present disclosure.

Rinsing solutions can be water, saline (NaCl, PBS, etc.), peroxides, alcohol (isopropyl, ethanol, etc.), crystalloids, sterilizing fluids (antibiotics such as gentamicin, vancomycin, bacitracin, polymixin, amphotericin, ampicillin, amikacin, teicoplanin, etc.), preserving fluids (DMEM, DMSO, mannitol, sucrose, glucose, etc.), storage agents, and/or other fluids used in processing of allografts. Reference is now made to FIG. 2, which depicts an alternative embodiment of the disclosure. Bone marrow is harvested from a cadaver, live donor, or harvested autologously from a patient in box 602. If a cadaver donor is used, a higher volume of marrow may be obtained by harvesting the marrow before any bone sectioning is done. In some embodiments, using a cannulated drill attached to a vacuum line to harvest marrow would also increase the yield of bone marrow from a cadaver donor. The tip of the cannulated drill breaks apart within the cancellous bone, allowing the vacuum to pull marrow through the cannula into a collection chamber.

Harvesting marrow from a living donor prior to the donor being removed from life support can also be employed as a marrow harvesting technique, because as the marrow is removed, blood flow caused by physiological circulation flushes additional bone marrow material into the area for further aspiration. After marrow has been harvested, particular cell types (such as mesenchymal stem cells, osteoblasts, osteocytes, or other progenitor cells) may be concentrated by filtration, centrifugation, magnetic bead binding, fluorescence activated cell sorting (FACS), and/or other cell sorting or concentration techniques as can be appreciated to increase the cell concentration, fractionate cell types, or eliminate particular cell types from the solution in box 604. Once, the desired cell population is obtained, it may be exposed to a lysis technique previously described, such as exposure to acetic acid in box 606.

Once acetic acid is added to the cells, they are given time to lyse and the growth factors and other bioactives are solubilized. The solution can be centrifuged or filtered to eliminated any cell fragments or cellular debris. The solution may undergo a second filtration step to remove other solid precipitates such as precipitated hemoglobin. The solution may undergo a third filtration step to concentrate the growth factors and other bioactives in the solution. The solution is then dehydrated by methods previously described, such as lyophilization. The solution is reduced to a water soluble powder in box 610 and may be sealed under vacuum to increase shelf-life in box 612. The solution can also be frozen to increase shelf life. This powder can be rich in a number or bioactive molecules and/or growth factors including, but not limited to, BMP-2, VEGF, aFGF, FGF-6, TGF-B1, and others as can be appreciated.

Figure 3:
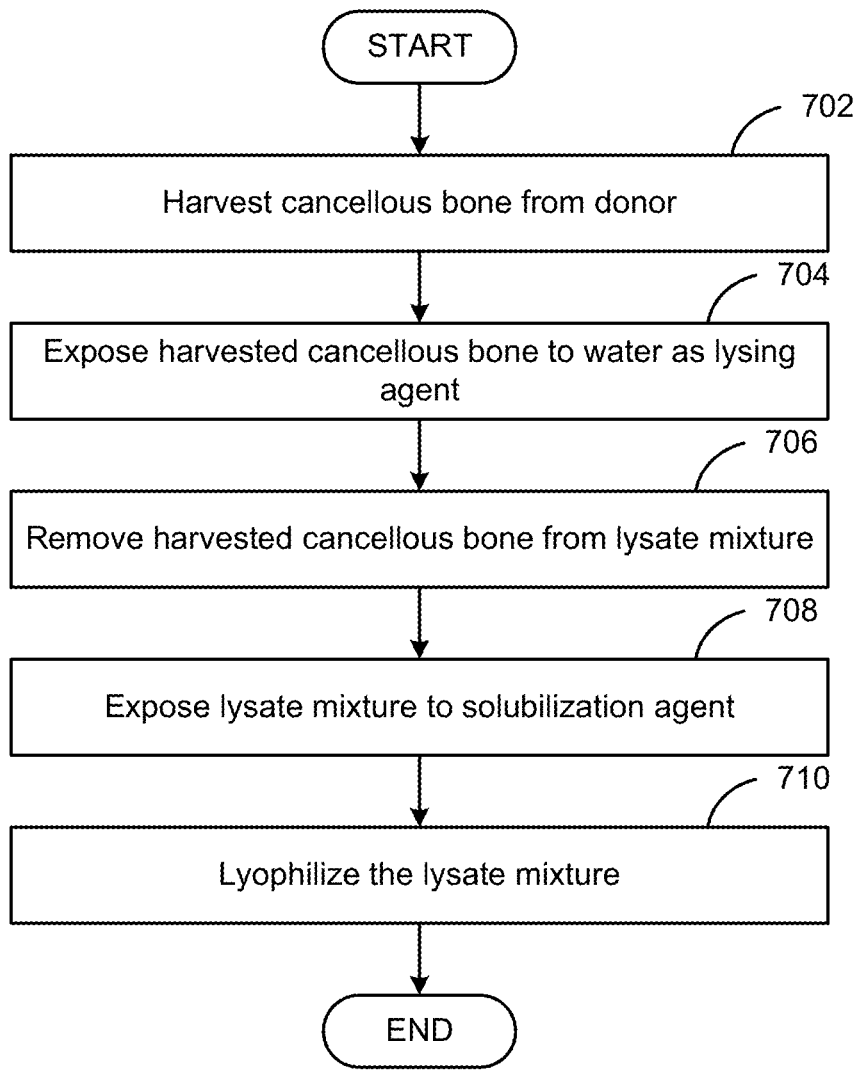
FIG. 3 is a flow diagram illustrating one embodiment in accordance with the present disclosure.

Reference is now made to FIG. 3, which depicts an alternative embodiment of the disclosure. In the depicted embodiment, cancellous bone is recovered from a cadaver, live donor, or harvested autologously from a patient in box 702. If required by a particular implant application, the harvested cancellous bone may be ground or cut to a desired shape and configuration. Care may be taken to retain as much bone marrow and blood within the bone during harvest and cutting operations. Cancellous bone may have cortical bone portions such as in the iliac crest, vertebral bodies, chondyles, etc. Accordingly, the cancellous bone may have cortical portions removed prior to further processing. The harvested cancellous bone is then exposed to a lysing agent, such as water, to lyse the cells contained in the cancellous bone in box 704. If a particular anticoagulant, such as heparin, is used as a lysing agent, the growth factors released by lysing the cells will be solubilized in solution. If no anticoagulant is used or if a different anticoagulant is used, such as sodium citrate, the cells will be lysed and release growth factors, but they will not be fully solubilized in the fluid.

In this case, the bone is then removed from the fluid in box 706 and a solubilization agent, such as an acid, is added to the fluid to solubilize the growth factors and other bioactives in box 708. Once the growth factors and other bioactives have been solubilized, the fluid may be neutralized and/or lyophilized in box 710. If acetic acid was used as the solubilizer, neutralization may be unnecessary as a substantial amount of acetic acid will vaporize during lyophilization. Alternatively, other lysing agents and solubilizers could be used to lyse the cells and solubilize the growth factors, preventing the growth factors and bioactive materials from binding to the cancellous bone from which the cells were harvested.

Figure 4:
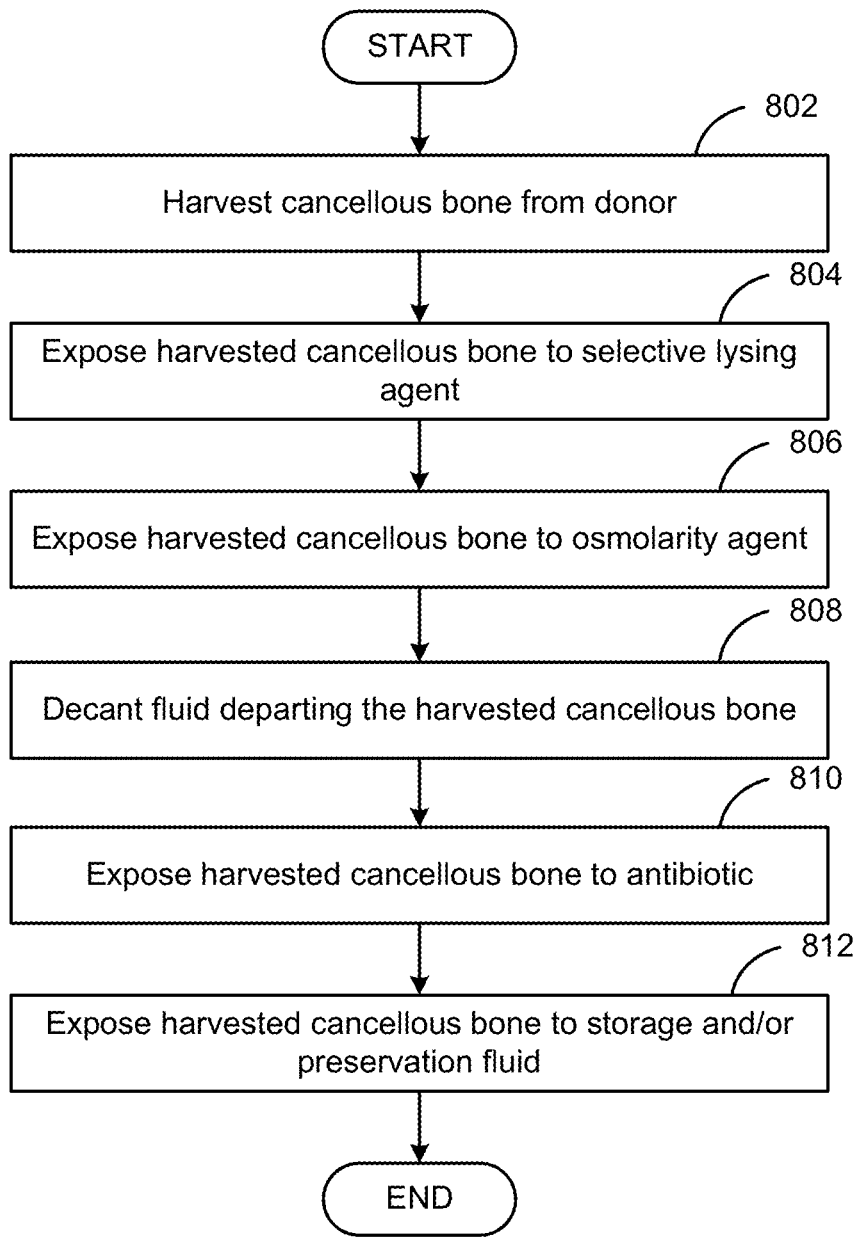
FIG. 4 is a flow diagram illustrating one embodiment in accordance with the present disclosure.

Reference is now made to FIG. 4, which depicts an alternative embodiment of the disclosure. In the depicted embodiment, cancellous bone is recovered from a cadaver, live donor, or harvested autologously from a patient in box 802. If required by a particular implant application, cancellous bone may be ground or cut to a desired shape and configuration. Care may be taken to retain as much bone marrow and blood within the bone during harvest and cutting operations. Cancellous bone may have cortical bone portions such as in the iliac crest, vertebral bodies, chondyles, etc. Accordingly, cortical portions of the harvested cancellous bone may be removed. The harvested cancellous bone is exposed to water to selectively lyse undesired cells types such as red blood cells, white blood cells, etc in box 804. In some embodiments, ratios of bone to water from 1 part bone to 1 part water and ranging to 1 part bone to 200 parts water can be employed. Any remaining viable cells that are not attached to the bone may be rinsed away in this fashion. Additionally, using a weak lysing agent (such as less then 1M acetic acid) may result in binding solubilized growth factors to the bone but still retaining viable progenitor cells attached to the bone.

The desired cells, such as mesenchymal stem cells, bone marrow stromal cells, progenitor cells, etc., remain viable in porous bone structure and on bone surface. Other mechanical lysing techniques previously described, such as sonication, stirring induced shear, thermolysis, etc., may be used in conjunction with the water bath to facilitate lysing of cellular material. After a lysing time (e.g., 1 minute-50 hours) has elapsed, saline is added to return osmolarity of the solution to physiological levels (e.g., approximately 0.9% salt) in box 806. After the solution is returned to isotonic conditions, the fluid is decanted leaving the bone in box 808. The effective rinse also facilitates removal of undesired cells unattached to the cancellous bone and discards them in the decanting step.

Antibiotics may be applied to the bone in box 810 to help with decreasing bioburden levels. Alternatively, in some embodiments antibiotics can be administered to the harvested cancellous bone prior to the lysing step. Some antibiotics that may be used include gentamicin, vancomycin, amphotericin, other antibiotics previously mentioned or as can be appreciated, or various antibiotics that can be used to reduce bioburden in allograft tissues. After the reduction of bioburden, the bone may be exposed to storage or preservation fluids such as DMEM, DMSO, sucrose, mannitol, glucose, etc., in box 812. The bone is then frozen until thawed for use in a surgical procedure to repair a skeletal defect. In some embodiments, the bone can be frozen at temperatures at or below −40 C.

Figure 5:
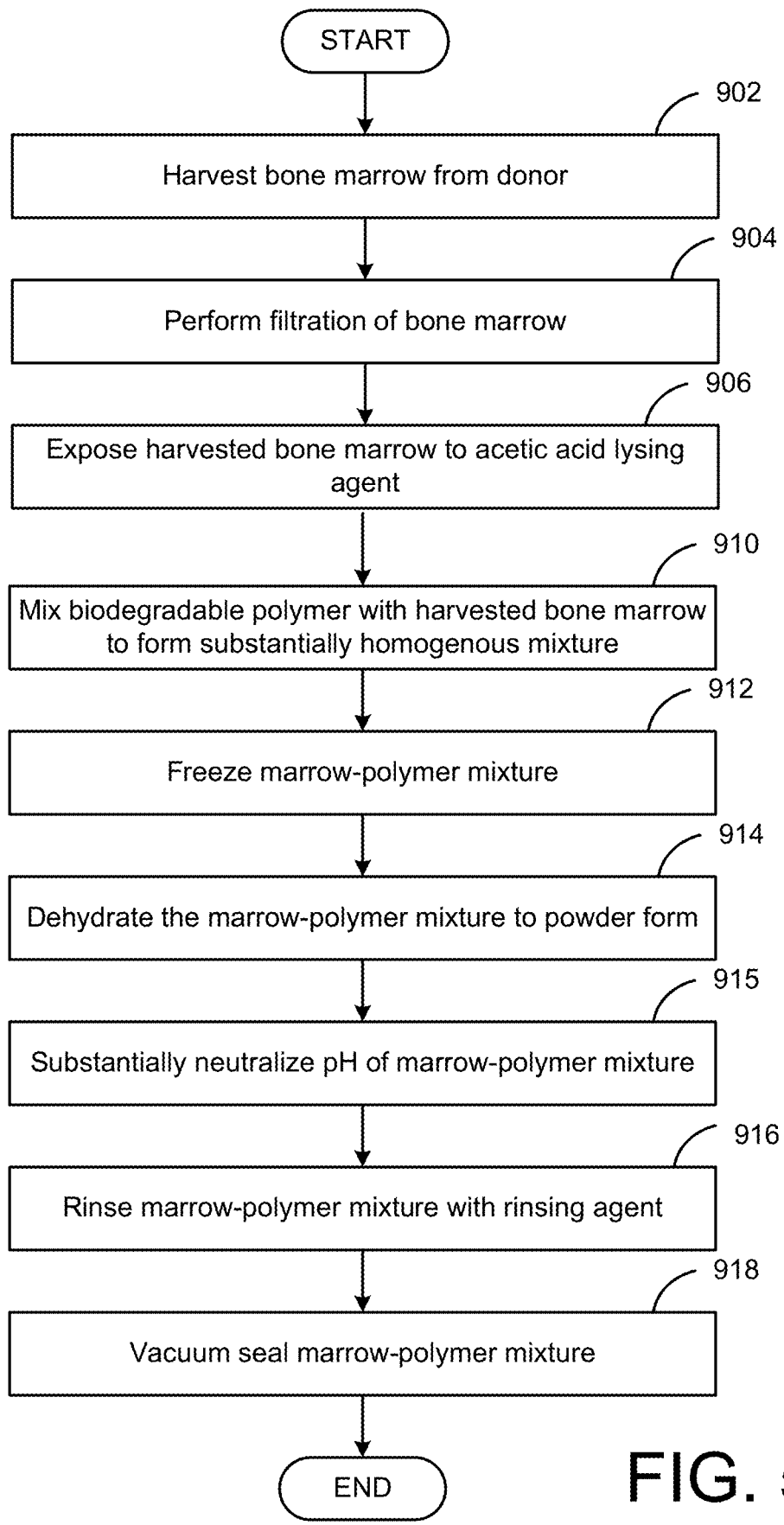
FIG. 5 is a flow diagram illustrating one embodiment in accordance with the present disclosure.

Reference is now made to FIG. 5, which depicts an alternative embodiment of the disclosure. In the depicted embodiment, the growth factors and bioactives obtained in the embodiments described above with reference to FIGS. 6 and/or 7 (as a non-limiting example) may be added to a biodegradable or resorbable polymer prior to dehydration. Accordingly, bone marrow harvested in box 902 can be subjected to at least one filtration process in box 904 as described above with reference to FIG. 2. The harvested bone marrow can be subjected to a lysing agent in box 906 as also described above.

In this embodiment, the growth factors and bioactives are harvested as previously described and added to a polymer with a common solvent, such as an acid. The biodegradable polymer may be a protein or polysaccharide, such as collagen, hyaluronan, chitosan, gelatin, etc., and combinations of two or more polymers. After the growth factors and bioactives are added to the polymer, it is mixed to obtain a substantially homogenous solution in box 910. Any bubbles or impurities may then be removed from the substantially homogenous solution. If other materials (such as, but not limited to, calcium phosphate, hydroxyapatite, heparin, chondroitin sulfate, etc.) are desired to be embedded into the implant for growth factor attachment, degradation by products, and/or mechanical reinforcement, they can also be added to the mixture.

The mixture is frozen in box 912 at a temperature that can range, in some embodiments, from −200 C to 0 C, to nucleate the water contained in the mixture into ice as well as condense the polymer/bioactive mixture into a porous structure. The mixture can be frozen in any geometry including, spherical, cylindrical, rectangular, in sheet form, tube form, etc. The implant will tend to retain this shape with its shape memory properties of the polymer is given space to expand in vivo. Temperatures can be increased to create larger pores or decreased to create small pores. Pores can be made directional by locating the cold temperature source substantially perpendicularly to the desired direction of the pores. Once the mixture is frozen at the desired temperature and pore direction, the implant is lyophilized and/or dehydrated in box 914 to substantially eliminate the water contained within it. If acetic acid or another volatile substance was used as the solvent, that solvent will also be substantially eliminated by lyophilization.

After the lyophilization cycle is complete, the scaffold may be substantially neutralized in ethanol, saline, base, or buffer depending on the solvent used as a lysing agent in box 915. In the case of an acetic acid solvent, the lyophilized implant may be rinsed in ethanol followed by saline or other rinsing agent in box 916. After the saline rinse, the implant may be rinsed free of salts with water and vacuum dried or lyophilized to extend shelf-life. The dehydrated implants may be packaged under vacuum or sealed in vacuum sealed vials in box 918. The implant can also be compressed prior to freezing and lyophilization or after neutralization and lyophilization to create a compacted scaffold that expands when exposed to fluid. Upon exposure to fluid, such an implant expands to substantially to approximately the original scaffold size. Delayed expansion may be achieved by compressing the neutralized scaffold and drying without freezing.

Figure 6:
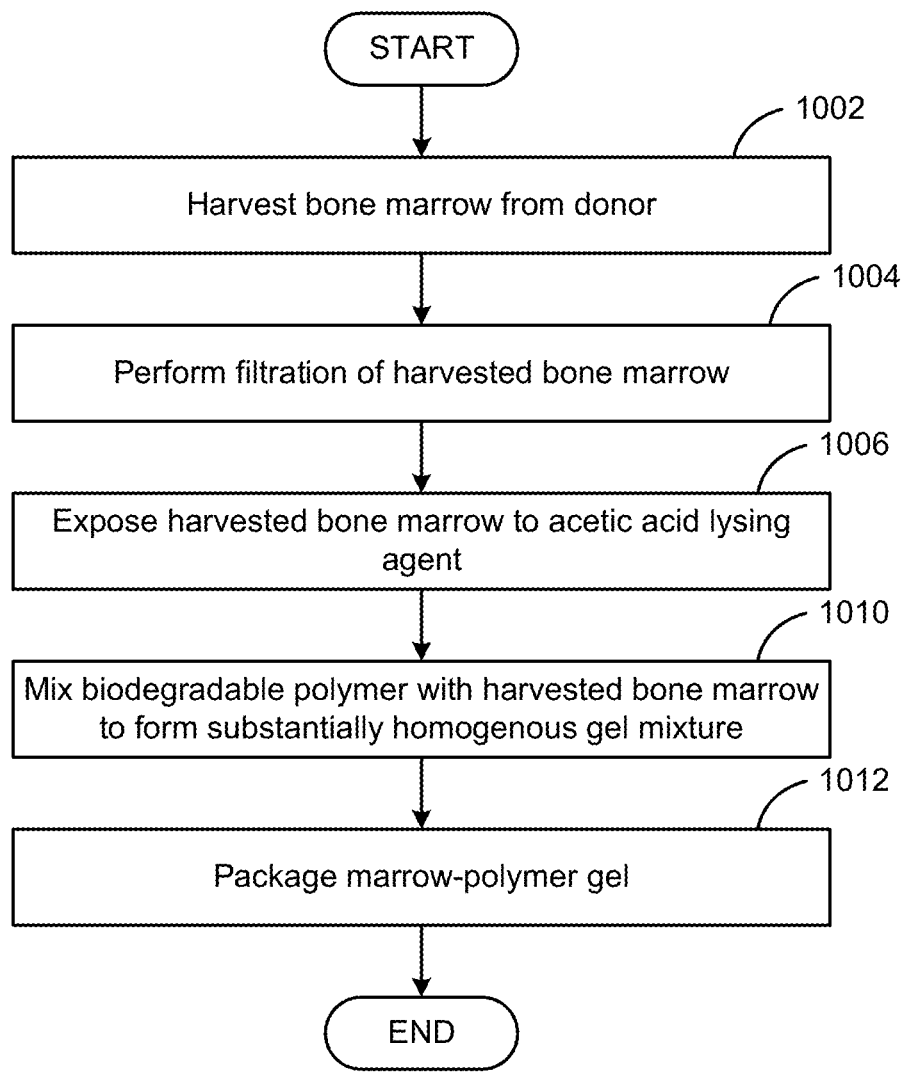
FIG. 6 is a flow diagram illustrating one embodiment in accordance with the present disclosure.

Reference is now made to FIG. 6, which depicts an alternative embodiment of the disclosure. In the depicted embodiment, the growth factors and/or bioactives obtained in the embodiments discussed with reference FIGS. 6 and 7 (as a non-limiting example) may be added to a biodegradable or resorbable polymer to create a flowable fluid and/or gel. In this embodiment, the growth factors and bioactives are harvested as previously described and added to a polymer with a common solvent, such as an acid. Accordingly, bone marrow harvested in box 1002 can be subjected to at least one filtration process in box 1004 as described above with reference to FIG. 62 The harvested bone marrow can be subjected to a lysing agent in box 1006 as also described above.

The biodegradable polymer may be a protein or polysaccharide, such as collagen, hyaluronan, chitosan, gelatin, etc., and combinations of two or more polymers. After the growth factors and bioactives are added to the polymer, it is mixed to obtain a substantially homogenous solution in box 1010. Any bubbles or impurities may be removed. If other materials (including, but not limited to, calcium phosphate, hydroxyapatite, heparin, chondroitin sulfate, etc.) are desired to be embedded into the implant for growth factor attachment, degradation by products, and/or mechanical reinforcement, they can also be added to the mixture.

A lysing agent can be chosen that is well tolerated by the body. For example, the growth factors and bioactives can be added to chitosan and in an acetic acid solution (0.01M-17M). The solution is mixed, and bubbles can be removed by applying vacuum or centrifugation. The gel can be packaged in syringes and either frozen and/or kept at ambient temperature in box 1012. Once injected and/or implanted into the body, the gel binds to tissue. Physiological fluids may buffer the gel to neutralize the pH and cause the gel to solidify in situ. Once the gel solidifies, the desired therapeutic implant remains in the intended surgical site and minimizes migration.

Figure 7:
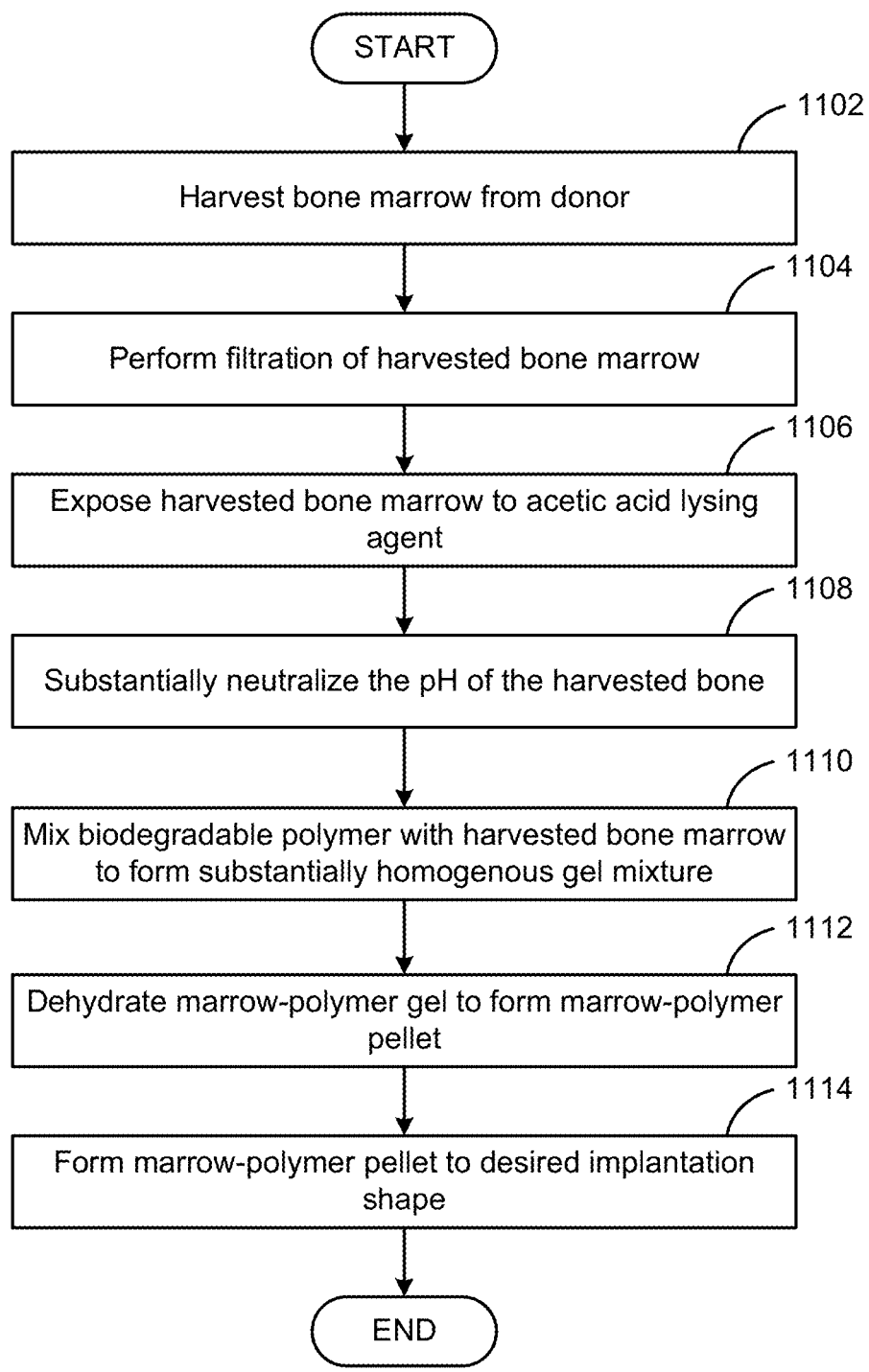
FIG. 7 is a flow diagram illustrating one embodiment in accordance with the present disclosure.
Figure 8:
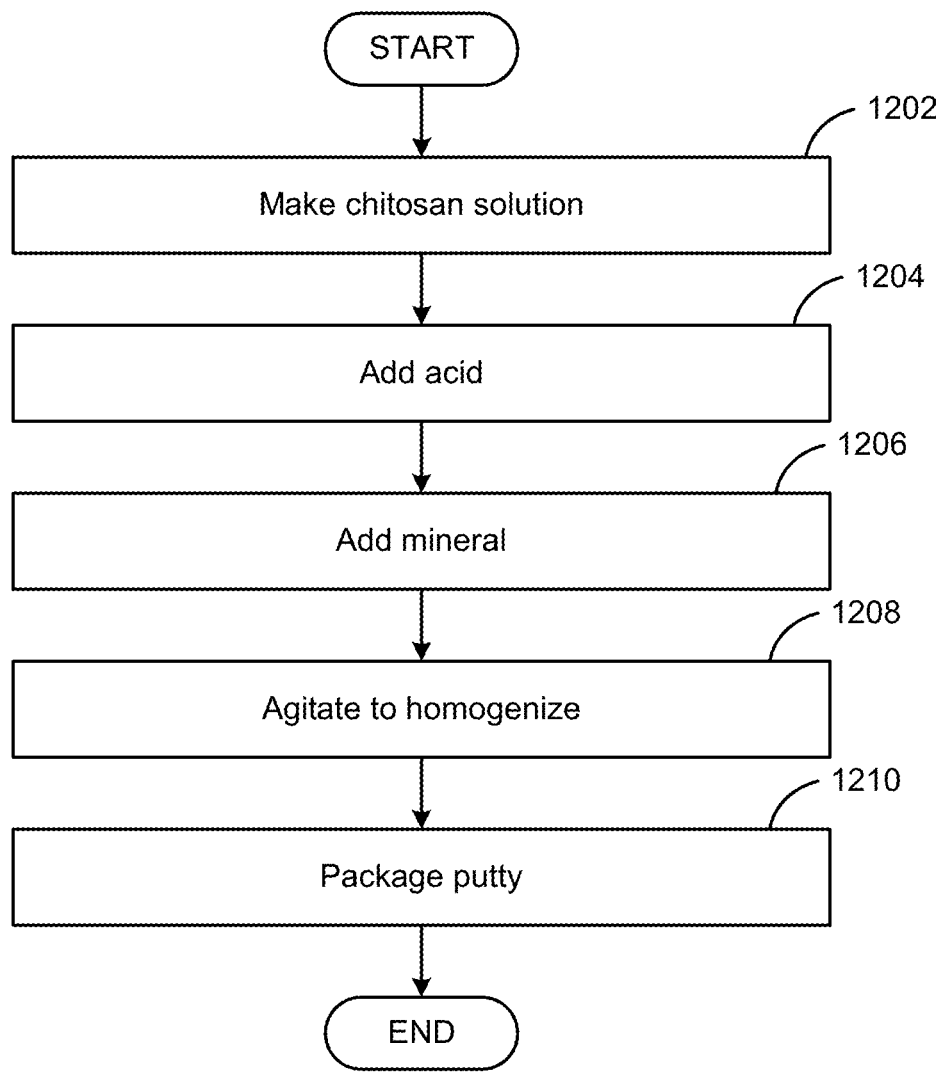
FIGS. 8-9 are flow diagrams illustrating methods to produce various embodiments of chitosan/mineral putty in accordance with the present disclosure.

Reference is now made to FIG. 7, which depicts an alternative embodiment of the disclosure. A gel obtained as described in the above embodiment discussed with reference to FIG. 6 may be dehydrated using techniques such as vacuum drying, solvent evaporation, etc., to reduce the gel into a semi-rigid film and/or pellet. Accordingly, bone marrow harvested in box 1102 can be subjected to at least one filtration process in box 1104 as described above with reference to FIG. 2. The harvested bone marrow can be subjected to a lysing agent in box 1106 as also described above.

The gel is dehydrated as described above in box 1112. The pellets may be ground further or cut into the desired particle size depending on a desired implant application in box 1114. Once exposed to fluid and implanted into the surgical site, the pellets and/or powder resulting from ground pellets form a cohesive putty that can also bind to tissue. This binding property keeps the putty substantially in place at the surgical site when implanted. This putty can be used as a bioactive surgical adhesive. The application of such a putty may also be advantageous when used with autologous materials used in surgical procedures, such as autograft bone used in spinal fusion procedures, because it may be beneficial to help keep the autograft in a cohesive mass and minimize migration.

Figure 9:
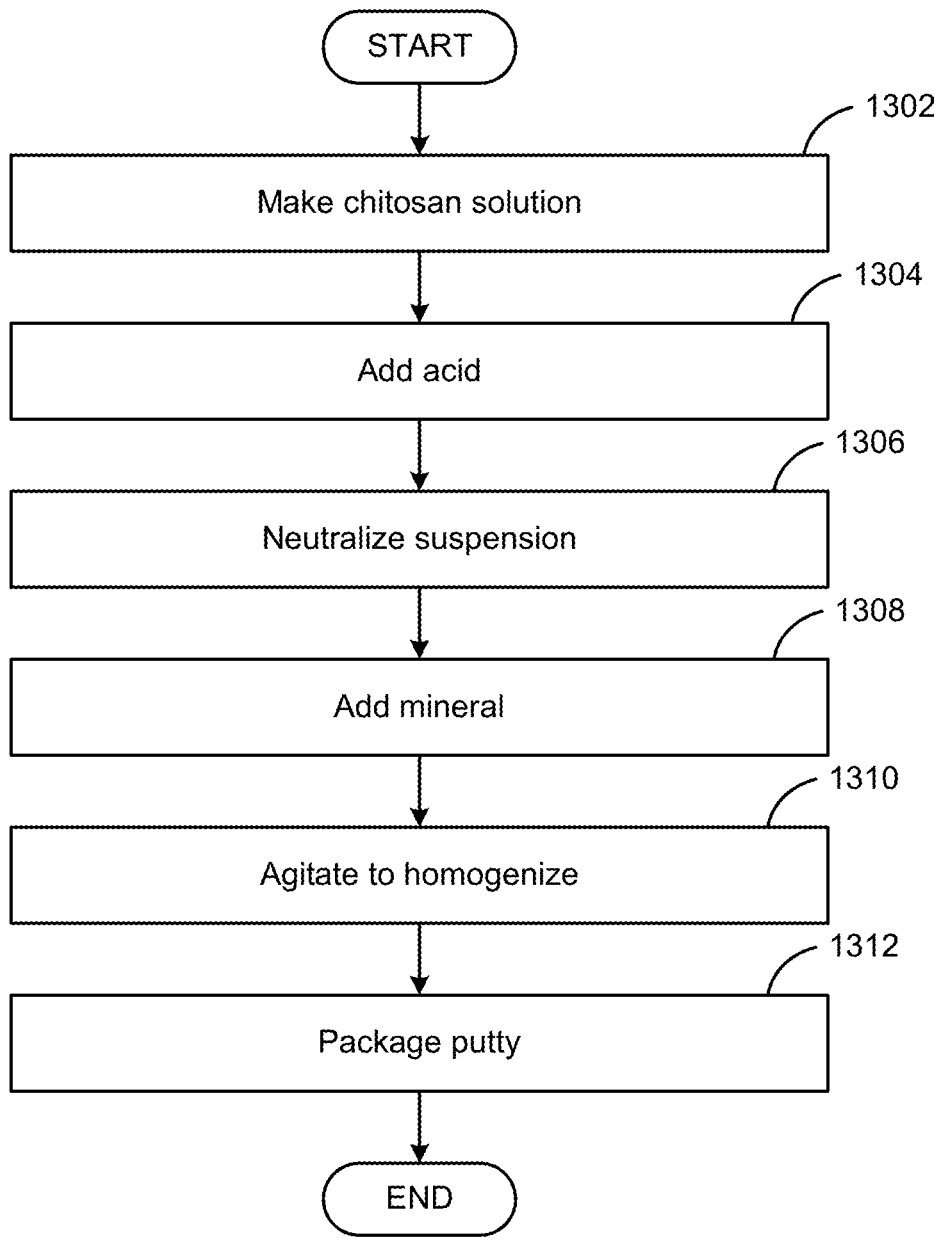

Referring now to FIG. 9, shown is a flow diagram illustrating a method to produce an embodiment of a low pH chitosan/mineral putty. In box 1202, a chitosan solution is made. The chitosan solution may be in the range of about 1% to about 25%. An acid (e.g., acetic acid) is then added in box 1204 to put the solution into a suspension. The acid may be in the range of about 0.1% to about 25%. A mineral in powder or granular form is then added in box 1206 and agitated to a homogenous mixture in box 1208. The putty is then packaged either wet or frozen in box 1210.

Referring next to FIG. 9, shown is a flow diagram illustrating a method to produce an embodiment of a neutral to partially neutral chitosan/mineral putty. In box 1302, a chitosan solution is made. The chitosan solution may be in the range of about 1% to about 25%. An acid (e.g., acetic acid) is then added in box 1304 to put the solution into a suspension. The acid may be in the range of about 0.1% to about 25%. The suspension is then neutralized or partially neutralized in box 1306 by adding base solution (e.g., sodium hydroxide or ammonium hydroxide) and agitating to homogenize the base solution. A mineral in powder or granular form is then added in box 1308 and agitated to a homogenous mixture in box 1310. The putty is then packaged either wet or frozen in box 1312.

Figure 10:
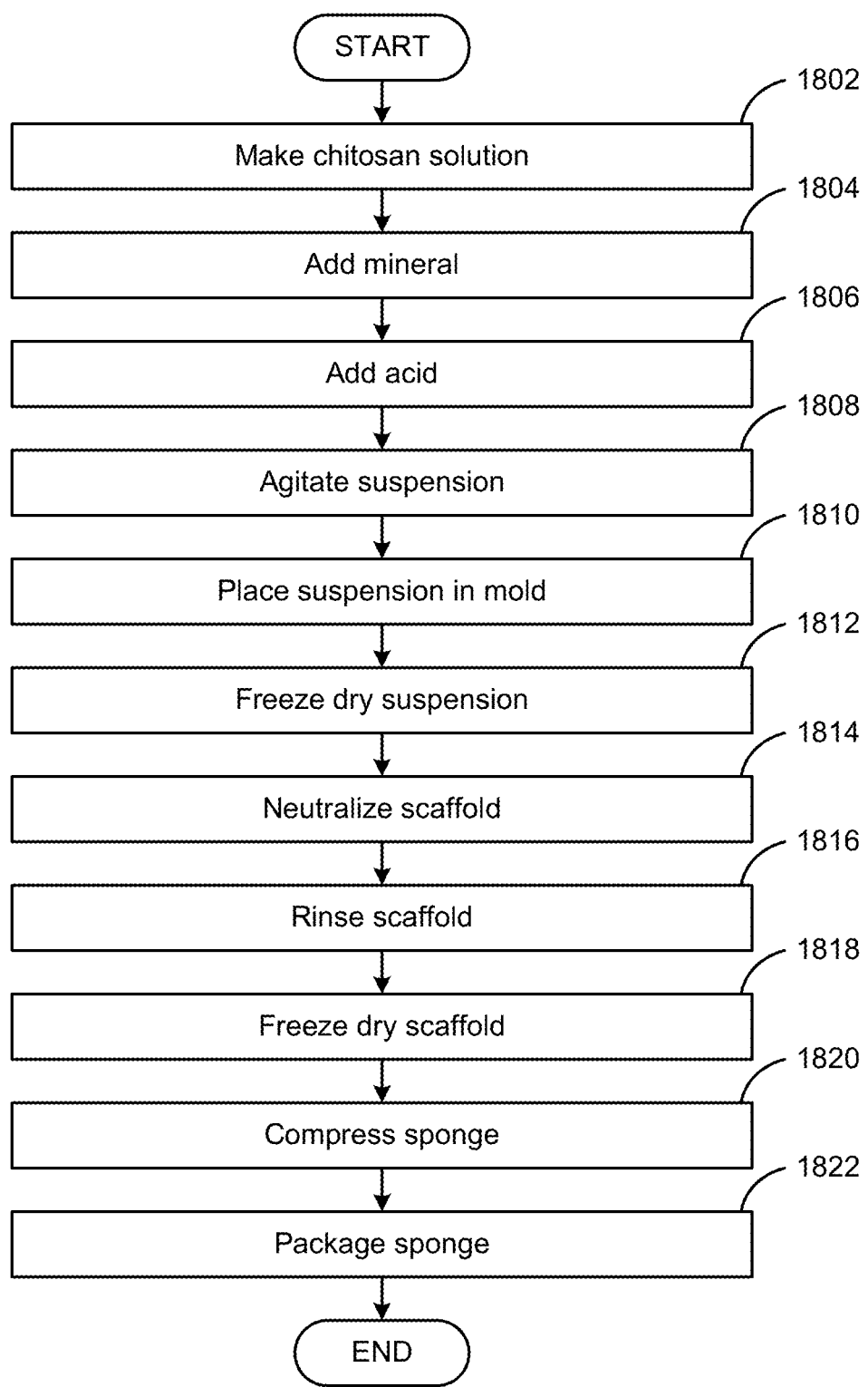
FIGS. 10-12 are flow diagrams illustrating methods to produce various embodiments of chitosan/mineral scaffold sponge in accordance with the present disclosure.

Referring now to FIG. 10, shown is a flow diagram illustrating a method to produce an embodiment of a neutral or partially neutral chitosan/mineral scaffold sponge. In box 1802, a chitosan solution is made. The chitosan solution may be in the range of about 1% to about 25%. A mineral in powder or granular form is then added in box 1804 and agitated to a homogenous mixture. An acid (e.g., acetic acid) is then added in box 1806 to put the solution into a suspension and agitated in box 1808. The acid may be in the range of about 0.1% to about 25%. The suspension is then placed into molds in box 1810 to conform to one or more desired shapes. The suspension is then freeze dried in box 1812. The molds are placed into a freezer and the suspensions are frozen to allow crystal formation. The frozen suspensions are lyophilized and the formed scaffolds are pulled out of molds. The scaffolds are then neutralized or partially neutralized in box 1814 by soaking in a base solution (e.g., sodium hydroxide or ammonium hydroxide). The scaffolds are then rinsed of any remaining base solution in sterile water or PBS in box 1816 and freeze dried in box 1818 where the scaffolds are frozen and lyophilized. The scaffolds are compressed into the desired shape in box 1820 and packaged and sterilized in box 1822.

Figure 11:
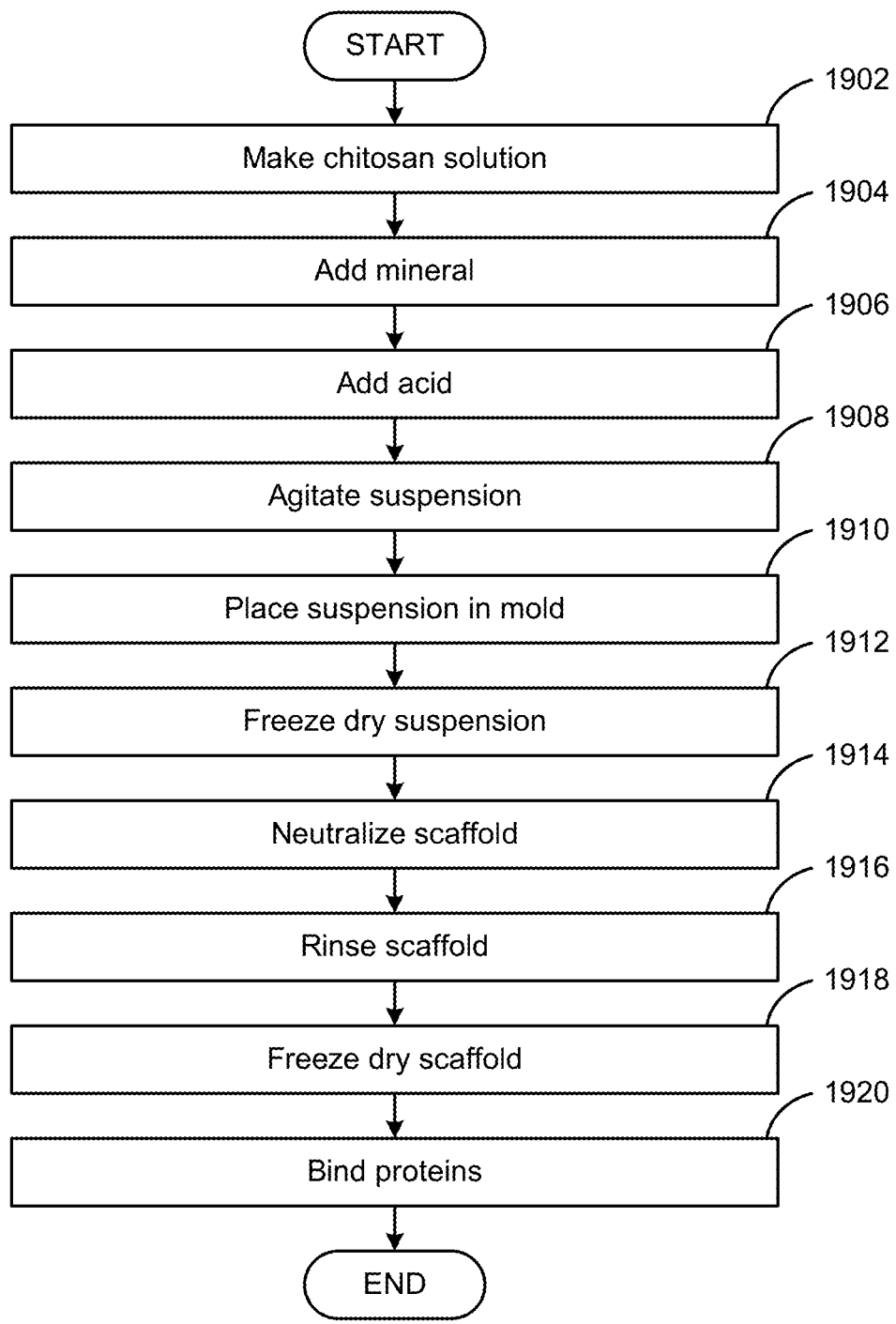

Referring next to FIG. 11, shown is a flow diagram illustrating a method to produce another embodiment of a neutral or partially neutral chitosan/mineral scaffold sponge. In box 1902, a chitosan solution is made. The chitosan solution may be in the range of about 1% to about 25%. A mineral in powder or granular form is then added in box 1904 and agitated to a homogenous mixture. An acid (e.g., acetic acid) is then added in box 1906 to put the solution into a suspension and agitated in box 1908. The acid may be in the range of about 0.1% to about 25%. The suspension is then placed into molds in box 1910 to conform to one or more desired shapes. The suspension is then freeze dried in box 1912. The molds are placed into a freezer and the suspensions are frozen to allow crystal formation. The frozen suspensions are lyophilized and the formed scaffolds are pulled out of molds. The scaffolds are then neutralized or partially neutralized in box 1914 by soaking in a base solution (e.g., sodium hydroxide or ammonium hydroxide). The scaffolds are then rinsed of any remaining base solution in sterile water or PBS in box 1916 and freeze dried in box 1918 where the scaffolds are frozen and lyophilized. Proteins are then bound onto the scaffold by way of soaking or vacuum perfusion in box 1920.

Figure 12:
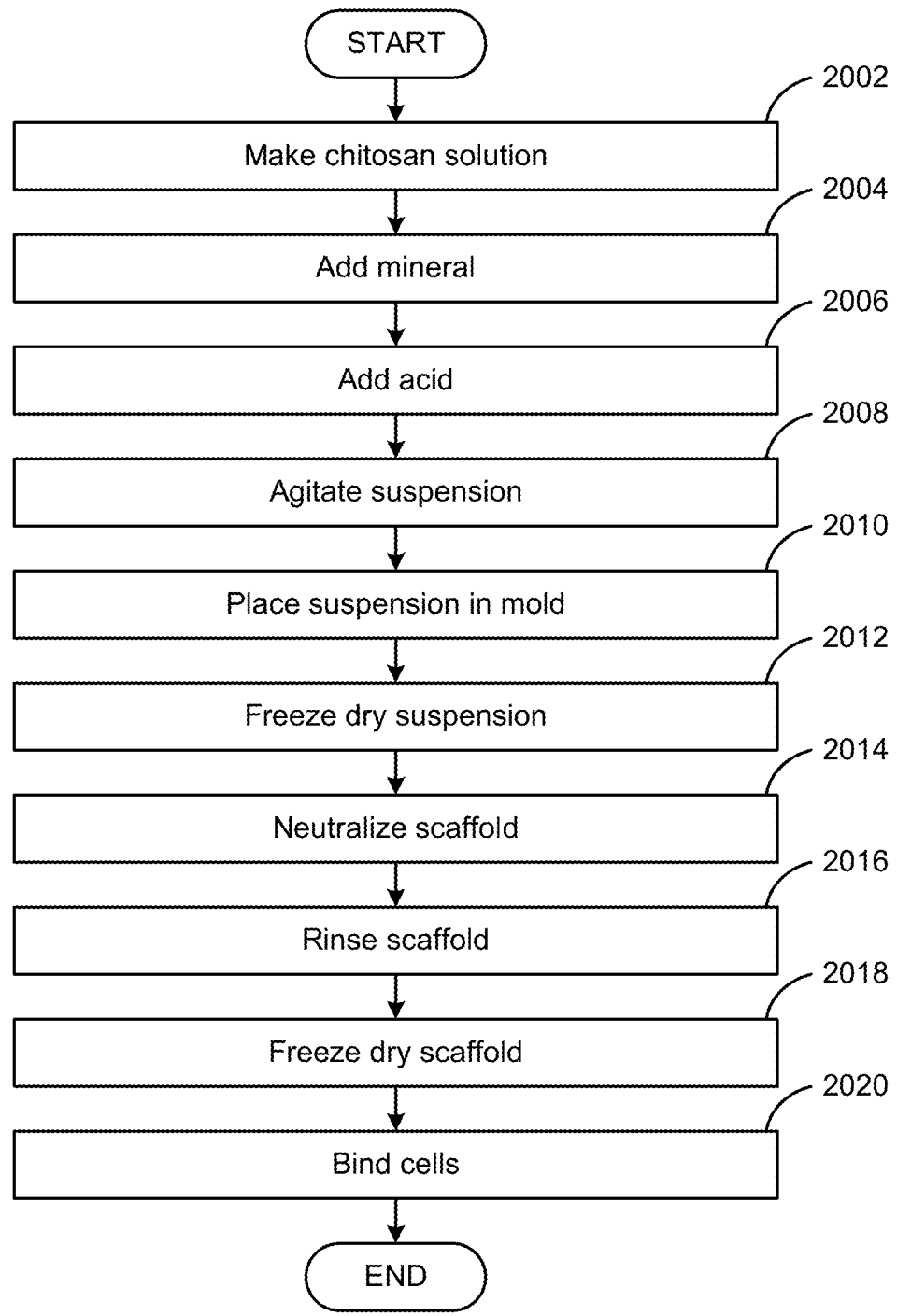

Reference is now made to FIG. 12, which depicts a flow diagram illustrating a method to produce an embodiment of a neutral or partially neutral chitosan/mineral scaffold sponge including seed cells. In box 2002, a chitosan solution is made. The chitosan solution may be in the range of about 1% to about 25%. A mineral in powder or granular form is then added in box 2004 and agitated to a homogenous mixture. An acid (e.g., acetic acid) is then added in box 2006 to put the solution into a suspension and agitated in box 2008. The acid may be in the range of about 0.1% to about 25%. The suspension is then placed into molds in box 2010 to conform to one or more desired shapes. The suspension is then freeze dried in box 2012. The molds are placed into a freezer and the suspensions are frozen to allow crystal formation. The frozen suspensions are lyophilized and the formed scaffolds are pulled out of molds. The scaffolds are then neutralized or partially neutralized in box 2014 by soaking in a base solution (e.g., sodium hydroxide or ammonium hydroxide). The scaffolds are then rinsed of any remaining base solution in sterile water or PBS in box 2016 and freeze dried in box 2018 where the scaffolds are frozen and lyophilized. Seed cells are then bound onto the scaffold by way of hydration, soaking or vacuum perfusion in box 2020.

Figure 13:
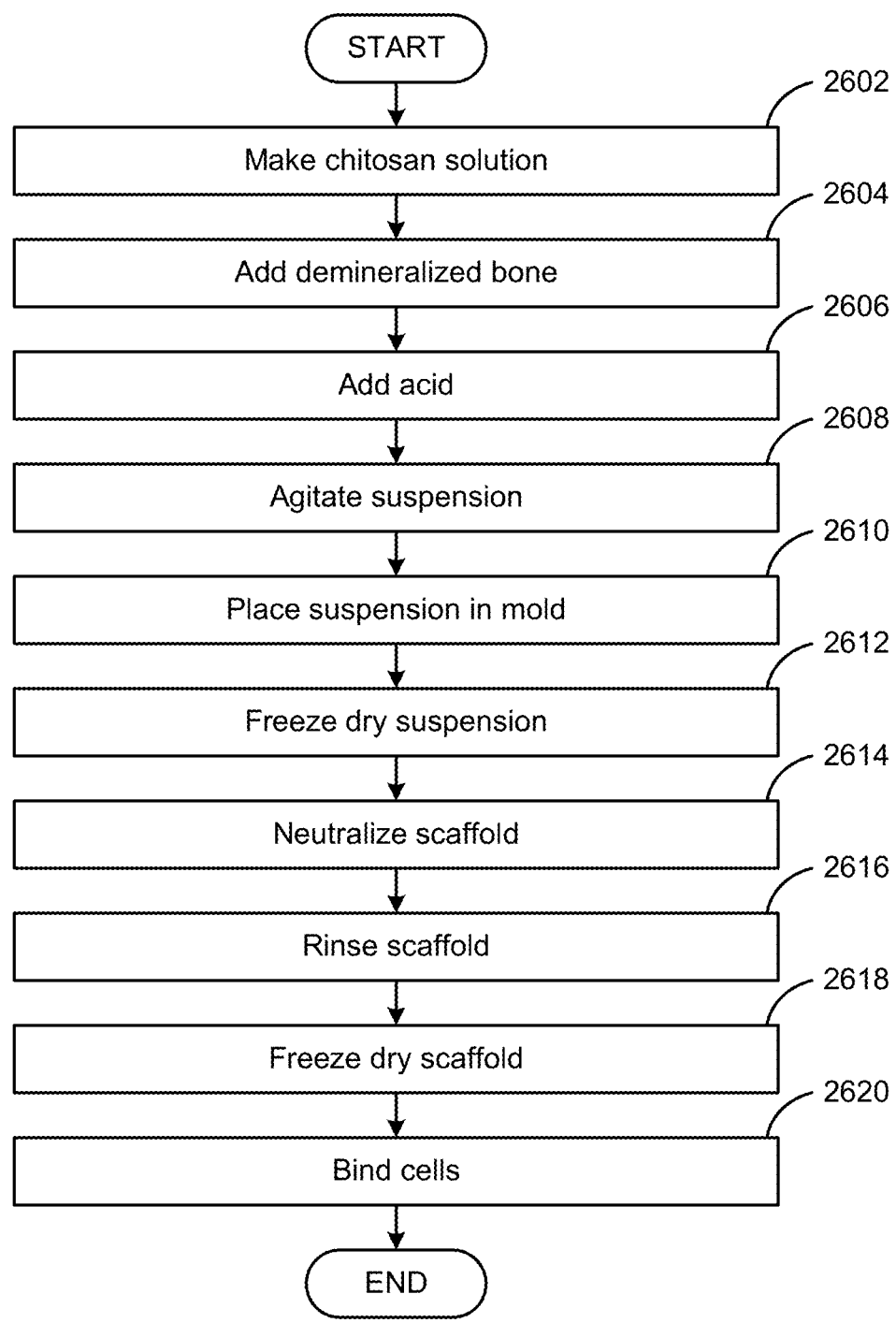
FIG. 13 is a flow diagram illustrating methods to produce various embodiments of a chitosan/bone scaffold sponge containing cells in accordance with the present disclosure.

Reference is now made to FIG. 13, which depicts a flow diagram illustrating a method to produce an embodiment of a neutral or partially neutral chitosan/demineralized bone scaffold sponge including seed cells. In box 2602, a chitosan solution is made. The chitosan solution may be in the range of about 1% to about 25%. Demineralized or partially demineralized bone in powder or granular form is then added in box 2604 and agitated to a homogenous mixture. An acid (e.g., acetic acid) is then added in box 2606 to put the solution into a suspension and agitated in box 2608. The acid may be in the range of about 0.1% to about 25%. The suspension is then placed into molds in box 2610 to conform to one or more desired shapes. The suspension is then freeze dried in box 2612. The molds are placed into a freezer and the suspensions are frozen to allow crystal formation. The frozen suspensions are lyophilized and the formed scaffolds are pulled out of molds. The scaffolds are then neutralized or partially neutralized in box 2614 by soaking in a base solution (e.g., sodium hydroxide or ammonium hydroxide). The scaffolds are then rinsed of any remaining base solution in sterile water or PBS in box 2616 and freeze dried in box 2618 where the scaffolds are frozen and lyophilized. Seed cells are then bound onto the scaffold by way of hydration, soaking or vacuum perfusion in box 2620. Once the cells are bound, the scaffolds may be packaged with a cryopreservative and frozen.

The following non-limiting examples are provided for further illustration.

Scaffold Sponge Formulation—Percent by Mass (Parts/100 Parts)

In a first non-limiting example, a solution of 6% of greater than 300 kDa molecular eight chitosan solution (>75% deacetylation) mixed in with 6% of tri-calcium phosphate (TCP) in 83.6% water was initially created. The solution was then mixed in with 4.4% of acetic acid to put the solution into suspension. The suspension was then placed into molds and frozen at a controlled rate by a ramp of 5° C. every 15 minutes to a temperature of −80° C. Once the suspension turned to a solid, the molds were lyophilized until drying was completed. The scaffolds were then hydrated with a 2 molar NaOH solution. Scaffolds were then rinsed with sterile water until reaching a neutral pH. Scaffolds were then frozen at a controlled rate and freeze dried to until dry.

In a second non-limiting example, a solution of 4% of greater than 300 kDa molecular weight chitosan solution (>75% deacetylation) mixed in with 6% of TCP in 85.6% water was initially created. The solution was then mixed in with 4.5% of acetic acid to put the solution into suspension. The suspension was then placed into molds and frozen at a controlled rate by a ramp of 5° C. every 15 minutes to a temperature of −80° C. Once the suspension turned to a solid, the molds were lyophilized until drying was completed. The scaffolds were then hydrated with a 2 molar NaOH solution. Scaffolds were then rinsed with sterile water until reaching a neutral pH. Scaffolds were then frozen at a controlled rate and freeze dried to till dry.

In a third non-limiting example, a solution of 3% of greater than 300 kDal molecular weight chitosan solution (>75% deacetylation) mixed in with 6% parts of TCP in 86.45% water was initially created. The solution was then mixed in with 4.55% of acetic acid to put the solution into suspension. The suspension was then placed into molds and frozen at a controlled rate by a ramp of 5° C. every 15 minutes to a temperature of −80° C. Once the suspension turned to a solid, the molds were lyophilized until drying was completed. The scaffolds were then hydrated with a 2 molar NaOH solution. Scaffolds were then rinsed with sterile water until reaching a neutral pH. Scaffolds were then frozen at a controlled rate and freeze dried to until dry.

In a fourth non-limiting example, a solution of 2% of greater than 300 kDa molecular weight chitosan solution (>75% deacetylation) mixed in with 6% of TOP in 87.4% water was initially created. The solution was then mixed in with 4.6% of acetic acid to put the solution into suspension. The suspension was then placed into molds and frozen at a controlled rate by a ramp of 5° C. every 15 minutes to a temperature of −80° C. Once the suspension turned to a solid, the molds were lyophilized until drying was completed. The scaffolds are then hydrated with a 2 molar NaOH solution. Scaffolds were then rinsed with sterile water until reaching a neutral pH. Scaffolds are then frozen at a controlled rate and freeze dried to until dry.

Sponge Formulation with Protein—Percent by Mass (Parts/100 Parts)

In a non-limiting example, a solution of 3% of greater than 300 kDa molecular weight chitosan solution (>75% deacetylation) mixed in with 6% parts of TOP in 86.45% water was initially created. The solution was then mixed in with 4.55% of acetic acid to put the solution into suspension. The suspension was then placed into molds and frozen at a controlled rate by a ramp of 5° C. every 15 minutes to a temperature of −80° C. Once the suspension turned to a solid, the molds were lyophilized until drying was completed. The scaffolds were then hydrated with a 2 molar NaOH solution. Scaffolds were then rinsed with sterile water until reaching a neutral pH. Scaffolds were then frozen at a controlled rate and freeze dried to until dry. The scaffolds were then fully saturated with protein solution.

Sponge Formulation with Cells—Percent by Mass (Parts/100 Parts)

In a non-limiting example, a solution of 3% of greater than 300 kDa molecular weight chitosan solution (>75% deacetylation) mixed in with 6% parts of TCP in 86.45% water was initially created. The solution was then mixed in with 4.55% of acetic acid to put the solution into suspension. The suspension was then placed into molds and frozen at a controlled rate by a ramp of 5° C. every 15 minutes to a temperature of −80° C. Once the suspension turned to a solid, the molds were lyophilized until drying was completed. The scaffolds were then hydrated with a 2 molar NaOH solution. Scaffolds were then rinsed with sterile water until reaching a neutral pH. Scaffolds were then frozen at a controlled rate and freeze dried to until dry. The scaffolds were then fully saturated with a physiological fluid containing viable cells.

Acidic Putty Formulation—Percent by Mass (Parts/100 Parts)

In a first non-limiting example, a solution of 1% of greater than 300 kDa molecular weight chitosan solution (>75% deacetylation) mixed in 45°/h water was initially created. The solution was then mixed in with 1% of acetic acid to put the solution into suspension. 53% of TCP was then added into the suspension and agitated until a homogeneous mixture was reached.

In a second non-limiting example, a solution of 1% of greater than 300 kDa molecular weight chitosan solution (>75% deacetylation) mixed in 44% water was initially created. The solution was then mixed in with 2% of acetic acid to put the solution into suspension. 53% of TCP was then added into the suspension and agitated until a homogeneous mixture was reached.

In a third non-limiting example, a solution of 1% of greater than 300 kDa molecular weight chitosan solution (>75% deacetylation) mixed in 43% water was initially created. The solution was then mixed in with 3% of acetic acid to put the solution into suspension. 53% of TOP was then added into the suspension and agitated until a homogeneous mixture was reached.

Neutral Putty Formulation—Percent by Mass (Parts/100 Parts)

In a non-limiting example, a solution of 1% of greater than 300 kDa molecular eight chitosan solution (>75% deacetylation) mixed in 45% water was initially created. The solution was then mixed in with 1% of acetic acid to put the solution into suspension. The suspension was then neutralized with 3°/h 2 molar NaOH solution and agitated. 53% of TCP was then added into the suspension and agitated until a putty-like consistency was reached.

Putty Formulation with Protein—Percent by Mass (Parts/100 Parts)

In a non-limiting example, a solution of 1% of greater than 300 kDa molecular weight chitosan solution (>75% deacetylation) mixed in 45% water was initially created. The solution was then mixed in with 1% of acetic acid to put the solution into suspension. The suspension was then neutralized with 3% 2 molar NaOH solution and agitated. 53% of TCP was then added into the suspension and agitated until a putty-like consistency was reached. The putty was then fully saturated with a protein solution.

Putty Formulation with Cells—Percent by Mass (Parts/100 Parts)

In a non-limiting example, a solution of 1% of greater than 300 kDa molecular weight chitosan solution (>75% deacetylation) mixed in 45% water was initially created. The solution was then mixed in with 1% of acetic acid to put the solution into suspension. The suspension was then neutralized with 3% 2 molar NaOH solution and agitated. 53% of TCP was then added into the suspension and agitated until a putty-like consistency was reached. The putty was then fully saturated with a physiological fluid containing viable cells.

Granular Powder Formulation—Percent by Mass (Parts/100 Parts)

In a non-limiting example, a solution of 2% of greater than 300 kDa molecular weight chitosan solution (>75% deacetylation) mixed in 45% water was initially created. The solution was then mixed in with 2% of acetic acid to put the solution into suspension. 51% of TCP was then added into the suspension and agitated until a putty-like consistency was reached. The putty was lyophilized and ground into a powder. The powder was mixed with autograft bone or a physiological fluid intraoperatively to create a gel or putty. The granular powder may be maintained as a powder for later reconstitution.

The chitosan/TCP scaffolds exhibited a porosity ranging from about 20 to about 80 μm. FIG. 14 provides examples of material properties of 41.13% and 20.42% material density scaffolds including volume of, material volume, empty space volume, and ROI.

Figure 15:
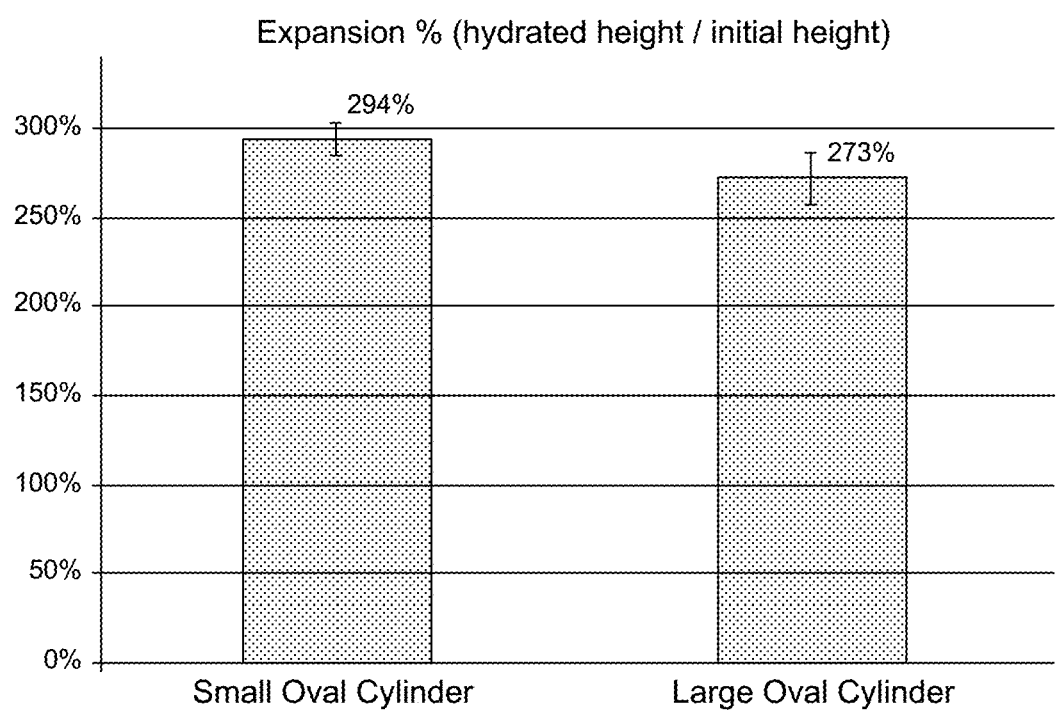
FIGS. 15-16 are graphs illustrating examples of scaffold expansion in accordance with various embodiments of the present disclosure.

Referring next to FIG. 15, shown is a graph for circumferential expansion in accordance with an exemplary embodiment of a scaffold. In this embodiment, the hydrated dimension was compared to the compressed dimension of the scaffold and the total expansion percentage was calculated based on a 30 mg/mL chitosan with 60 mg/mL TCP formulation.

Figure 16:
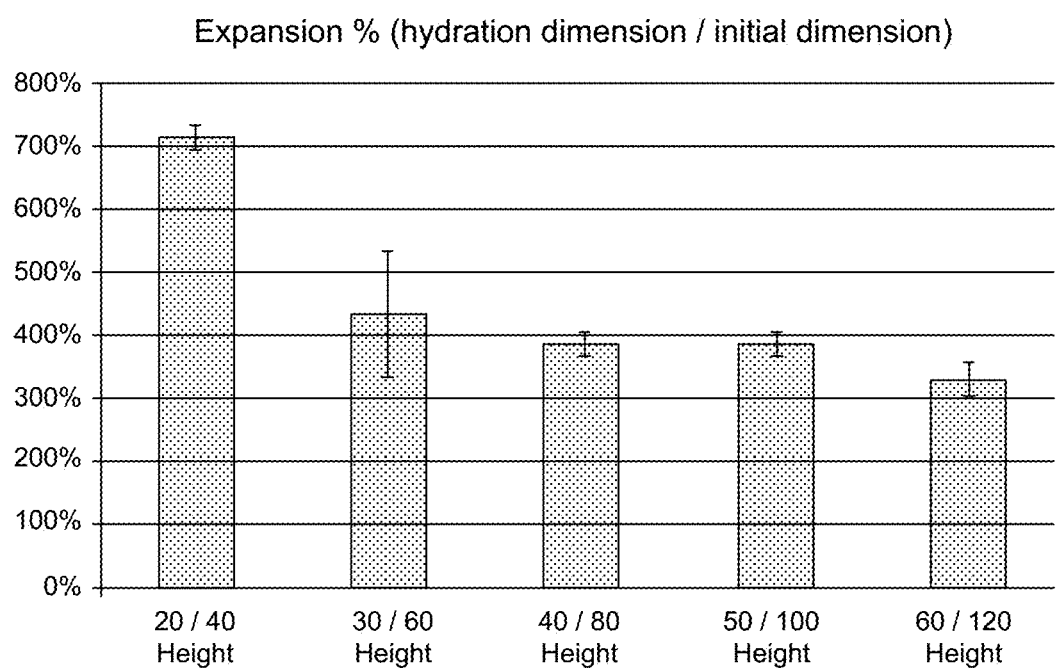

Referring next to FIG. 16, shown is a graph for uniaxial expansion in accordance with an exemplary embodiment of a scaffold. In this embodiment, the hydrated dimension was compared to the compressed dimension of the scaffold. Total expansion percentages were calculated for different formulations including chitosan concentrations of 20, 30, 40, 50, and 60 mg/mL corresponding to tri-calcium phosphate concentrations of 40, 60, 80, 100, and 120 mg/mL, respectively.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

Although the flowcharts depicted in the included drawings show a specific order of execution of the various steps, it is understood that the order of execution may differ from that which is depicted. For example, the order of execution of two or more blocks may be scrambled relative to the order shown. Also, two or more blocks shown in succession may be executed concurrently or with partial concurrence. It should be emphasized that the above-described embodiments of the present disclosure are merely possible examples of implementations set forth for a clear understanding of the principles of the disclosure.

We claim:

1. An implant comprising:
   cortical allograft bone and cancellous allograft bone obtained from an allograft donor, wherein the cancellous allograft bone is processed by a method comprising:
   osmotically lysing bone marrow cells in the allograft cancellous bone to enrich for cells resistant to osmotic lysing, wherein the step of osmotically lysing comprises exposing the allograft cancellous bone to water or less than 1M acetic acid, and
   during and following the lysing, allowing both the cells resistant to the lysing and growth factors released from the cancellous allograft bone to bind to the cancellous and cortical allograft bones;
   when implanted, the implant comprises the cells resistant to lysing and the growth factors each associated with the allograft cancellous bone.

2. The implant of claim 1, further comprising an antibiotic.

3. The implant of claim 1, a portion of the growth factors released from the cancellous allograft bone are bound to the cortical bone, wherein the growth factors are obtained from the allograft donor.

4. The implant of claim 3, wherein the growth factors are obtained from the osmotically bone marrow cells in the cancellous allograft bone.

5. The implant of claim 3, wherein the growth factors comprise bone morphogenetic protein.

6. The implant of claim 1, wherein the cortical allograft bone is demineralized.

7. The method of claim 1, wherein the cortical allograft bone is in the form of a fiber.

8. The implant of claim 1, wherein the cortical allograft bone is in the form of particulates.

9. The implant of claim 1, wherein the cells resistant to osmotic lysing comprise mesenchymal stem cells, bone marrow stromal cells, and progenitor cells.

10. The implant of claim 1, wherein at least one of the cells resistant to osmotic lysing is viable.

11. The implant of claim 4, further comprising a step of attaching the released growth factors to the cortical bone.

12. The implant of claim 11, wherein the released growth factors comprise bone morphogenetic proteins.

* * * * *